United States Patent [19]
Nyce

[11] Patent Number: 6,025,339
[45] Date of Patent: *Feb. 15, 2000

[54] COMPOSITION, KIT AND METHOD FOR TREATMENT OF DISORDERS ASSOCIATED WITH BRONCHOCONSTRICTION AND LUNG INFLAMMATION

[75] Inventor: Jonathan W. Nyce, Greenville, N.C.

[73] Assignee: East Carolina University, Greenville, N.C.

[*] Notice: This patent is subject to a terminal disclaimer.

[21] Appl. No.: 08/757,024

[22] Filed: Nov. 26, 1996

Related U.S. Application Data

[63] Continuation-in-part of application No. 08/472,527, Jun. 7, 1995.

[51] Int. Cl.$^7$ .......................... A61K 48/00; C12N 15/11; C12N 15/09
[52] U.S. Cl. ................ 514/44; 435/6; 435/69.1; 435/172.3; 536/24.5; 935/33; 935/65
[58] Field of Search .......................... 435/6, 69.1, 172.3, 435/91.1; 514/44; 935/62, 55, 56, 34, 54, 52, 70, 71, 66, 65; 536/24.5

[56] References Cited

U.S. PATENT DOCUMENTS

| | | | |
|---|---|---|---|
| 5,225,326 | 7/1993 | Bresser et al. | 435/6 |
| 5,245,022 | 9/1993 | Weis et al. | 536/24.5 |
| 5,320,962 | 6/1994 | Stiles et al. | 435/252.3 |
| 5,585,479 | 12/1996 | Hoke et al. | 536/24.5 |

FOREIGN PATENT DOCUMENTS

| | | | |
|---|---|---|---|
| 2264948 | 9/1993 | United Kingdom | C07K 13/00 |
| WO 93/25677 | 12/1993 | WIPO | C12N 15/12 |
| 94/02605 | 3/1994 | WIPO. | |

OTHER PUBLICATIONS

Stull et al. "Antigene, Ribozyme and Aptamer Nucleic Acid Drugs: Progress and Prospects," Pharmaceutical Research, vol. 12, No. 4: 46j5–483, 1995.

Miller et al. "Gene Transfer and Antisense Nucleic Acid Techniques," Parasitology Today, vol. 10, No. 3: 92–97, 1994.

Wu Pong, S. "Oligonucleotides: Opportunities for Drug Therapy and Research," Pharmaceutical Technology, vol. 18: 102–114, Oct. 1994.

Nyce, J.W., "Respirable Antisense Oligonucleotides as Novel Therapeutic Agents for Asthma and Other Pulmonary Diseases", *Exp. Opin. Invest. Drugs*, 6(9): 1–7, (1997).

Nyce, J.W. et al., "DNA Antisense Therapy for Asthma in an Animal Model", *Nature*, 385(20): 721–725, (1997).

Akhter, S. et al., "In Vivo Studies with Antisense Oligonucleotides", *Trends in Pharmacol. Sciences*, 18: 12–18, (1997).

Webb, A. et al., "BCL–2 Antisense Therapy in Patients with Non–Hodgkin Lymphoma", *Lancet*, 349(9059): 1137–41, (1997).

Yazaki, T. et al., "Treatment of Glioblastoma U–87 by Systemic Administration of an Antisense Protein Kinase C–Alpha Phosphorothioate Oligodeoxynucleotide", *Molecular Pharmacol.*, 50(2): 236–242, (1996).

Farmer, S.G. et al., "Adenosine Receptor–mediated Contraction and Relaxation of Guinea–pig Isolated Tracheal Smooth Muscle: Effects of Adenosine Antagonists", *Br. J. Pharmacol.*, 95: 371–378 (1988).

Marquardt, D.L. et al., "Aminophylline Exposure Alters Mouse Bone Marrow–derived Mast Cell Adenosine Responsiveness", *J. Allergy Clin Immunol.* 78: 462–469, (1986).

J. Milligan et al.; Current Concepts in Antisense Drug Design. *J. Med. Chem.* 36(14): 1923–1937 (1993).

S. Ali et al.; Adenosine–induced bronchoconstriction in an allergic rabbit model:antagonism by theophylline aerosol. *Agents Actions* 37:165–167 (1992).

S. Ali et al.; Modification of allergen–induced airway obstruction and bronchial hyperresponsiveness in the allergic rabbit by theophylline aerosol. *Agents Actions* 37:168–170 (1992).

S. Ali et al.; Adenosine–Induced Bronchoconstriction and Contraction of Airway Smooth Muscle from Allergic Rabbits with Late–Phase Airway Obstruction: Evidence for an Inducible Adenosine $A_1$ Receptor. *J. Pharmacol. Exp. Therapeu.* 268:1328–1334 (1994).

S. Ali et al.; Adenosine receptor–mediated bronchoconstriction and bronchial hyperresponsiveness in allergic rabbit model. *Am. J. Physiol.* 266:L271–277 (1994).

D.R. Sibley, et al; Transfected Mammalian Cell Lines Expressing the A1 Adenosine Receptor *NTIS Field/Group Codes: 57F, 57B, 57Q 90D* (Jun. 5, 1991).

*Primary Examiner*—Brian R. Stanton
*Assistant Examiner*—Karen M. Hauda
*Attorney, Agent, or Firm*—Viviana Amzel

[57] ABSTRACT

A method of reducing bronchoconstriction in a subject in need of such treatment is disclosed. The method comprises administering to the subject an antisense oligonucleotide molecule directed against the $A_1$ or $A_3$ adenosine receptor in an amount effective to reduce bronchoconstriction. The method is useful for treating patients afflicted with asthma. Pharmaceutical formulations are also disclosed.

77 Claims, No Drawings

COMPOSITION, KIT AND METHOD FOR TREATMENT OF DISORDERS ASSOCIATED WITH BRONCHOCONSTRICTION AND LUNG INFLAMMATION

RELATED APPLICATIONS

This application is a continuation-in-part of U.S. Application Ser. No. 08/472,527, filed 07 Jun. 1995.

This invention was made at least partially with United States Government support under grant RO1CA47217-06 from the National Cancer Institute. The Government may have certain rights to this invention.

BACKGROUND OF THE INVENTION

1. Field of the Invention

This application concerns a method of administering antisense oligonucleotides against the $A_1$ and $A_3$ Adenosine receptors as a treatment for asthma.

2. Description of the Background

Asthma is one of the most common diseases in industrialized countries, and in the United States accounts for about 1% of all health care costs. K. Weiss et al., *New Engl. J. Med.* 326, 862–866 (1992). There has been reported an alarming increase in both the prevalence and mortality of asthma over the past decade, Asthma—United States, 1980–1990, *MMWR* 41, 733–735 (1992), and occupational asthma is predicted to be the preeminent occupational lung disease in the next decade. M. Chan-Yeung and J. Malo, *European Resp. J.* 7, 346–371 (1994). While the increasing mortality from asthma in industrialized countries might be attributable to the increased reliance upon beta agonists in the treatment of this disease, the underlying causes of asthma remain poorly understood. J. Gern and R. Lemanske, In *Immunology and Allergy Clinics of North America* 13, Bush, R. K. ed. W. B. Saunders Company, London, pp. 839–860 (1993).

Adenosine may constitute an important natural mediator of bronchial asthma. R. Pauwels et al., *Clinical & Exp. Allergy* 21 Suppl. 1, 48–55 (1991); S. Holgate et al., *Annals of the New York Acad. Sci.* 629, 227–236 (1991). The potential role of adenosine in human asthma is supported by the experimental finding that, in contrast to normal individuals, asthmatic individuals respond to aerosolized adenosine with marked bronchoconstriction. M. Church and S. Holgate, *Trends Pharmacol. Sci.* 7, 49–50 (1986); M. Cushley et al., *Br. J. Clin. Pharmacol.* 15, 161–165 (1983). Similarly, asthmatic rabbits produced using the dust mite allergic rabbit model of human asthma also were shown to respond to aerosolized adenosine with marked bronchoconstriction, while non asthmatic rabbits showed no response. S. Ali et al., *Agents Actions* 37, 165–176 (1992). Recent work using this model system has suggested that adenosine-mediated bronchoconstriction and bronchial hyperresponsiveness in asthma are mediated primarily through the stimulation of adenosine receptors. S. Ali et al., *J. Pharmacol. Exp. Ther.* 268, 1328–1334 (1994); S. Ali et al., *Am. J. Physiol* 266, L271–277 (1994).

Theophylline, an important drug in the treatment of asthma, is a known adenosine receptor antagonist (see M. Cushley et al., *Am. Rev. Resp. Dis.* 129, 380–384 (1984)) and was found to eliminate adenosine-mediated bronchoconstriction in asthmatic rabbits (Ali, et al., supra). The pretreatment of allergic rabbits with another A1-specific receptor antagonist, 8-cyclopentyl-1,3-dipropylxanthine (DPCPX), potently inhibited adenosine-mediated bronchoconstriction and bronchial hyperresponsiveness in allergic rabbits. Id. The therapeutic potential, however, of currently available adenosine $A_1$ receptor-specific antagonists is limited by their toxicity. H. Klitgaard et al., *European J. Pharmacol.* 242, 221–228 (1993). Theophylline has been widely used in the treatment of asthma, but is associated with frequent, significant toxicity resulting from its narrow therapeutic dose range. E. Powell et al., *Pediatric Emergency Care* 9, 129–133 (1993); S. Nasser and P. Rees, *Drug Safety* 8, 12–18 (1993); P. Epstein, *Annals of Internal Med.* 119, 1216–1217 (1993). The availability of an alternative strategy to downregulate adenosine-mediated bronchoconstriction would clearly be of therapeutic interest.

SUMMARY OF THE INVENTION

The present invention relates to a method of reducing adenosine-mediated bronchoconstriction in a subject in need of such treatment. The method comprises administering an adenosine receptor antisense oligonucleotide to the lungs of the subject in an amount effective to reduce bronchoconstriction, where the adenosine receptor is selected from the group consisting of $A_1$ adenosine receptors and $A_3$ adenosine receptors.

The present invention relates to a method of treating asthma in a subject in need of such treatment. The method comprises administering an adenosine receptor antisense oligonucleotide to the lungs of the subject in an amount effective to treat asthma, where the adenosine receptor is selected from the group consisting of $A_1$ adenosine receptors and $A_3$ adenosine receptors.

Also part of the present invention is a pharmaceutical composition, comprising, a pharmaceutically acceptable carrier, and an adenosine receptor antisense oligonucleotide. The adenosine receptor is selected from the group consisting of the adenosine $A_1$ and $A_3$ receptors.

The antisense oligonucleotide of this invention may be applied to the preparation of a medicament for (a) reducing adenosine-mediated bronchoconstriction in a subject in need of such treatment, or (b) treating asthma in a subject in need of such treatment.

Antisense oligonucleotides have received considerable theoretical consideration as potentially useful pharmacologic agents in human disease. R. Wagner, *Nature* 372, 333–335 (1994). However, practical applications of these molecules in actual models of human disease have been elusive. One important consideration in the pharmacologic application of these molecules is route of administration. Most experiments utilizing antisense oligonucleotides in vivo have involved direct application to limited regions of the brain (see C. Wahlestedt, *Trends in Pharmacological Sciences* 15, 42–46 (1994); J. Lai et al., *Neuroreport* 5, 1049–1052 (1994); K. Standifer et al., *Neuron* 12, 805–810 (1994); A. Akabayashi et al., *Brain Research* 21, 55–61 (1994)), or to spinal fluid (see e.g. L. Tseng et al., *European J. Pharmacol.* 258, R1-3 (1994); R. Raffa et al., *European J. Pharmacol.* 258, R5-7 (1994); F. Gillardon et al., *European J. Neurosci.* 6, 880–884 (1994)). Such applications have limited clinical utility due to their invasive nature.

The systemic administration of antisense oligonucleotides also poses significant problems with respect to pharmacologic application, not the least of which is the difficulty in targeting disease-involved tissues. In contrast, the lung is an excellent potential target for antisense oligonucleotide application since it may be approached noninvasively and in a tissue-specific manner.

DETAILED DESCRIPTION OF THE INVENTION

Nucleotide sequences are presented herein by single strand only, in the 5' to 3' direction, from left to right.

Nucleotides and amino acids are represented herein in the manner recommended by the IUPAC-IUB Biochemical Nomenclature Commission, or (for amino acids) by three letter code, in accordance with 37 CFR §1.822 and established usage. See, e.g., *PatentIn User Manual*, 99–102 (November 1990) (U.S. Patent and Trademark Office, Office of the Assistant Commissioner for Patents, Washington, D.C. 20231); U.S. Pat. No. 4,871,670 to Hudson et al. at Col. 3 lines 20–43. The relevant sections of the disclosures of this and all other patents and other references cited in this patent be incorporated herein by reference.

The method of the present invention may be used to reduce adenosine-mediated bronchoconstriction in the lungs of a subject for any reason, including (but not limited to) asthma. Antisense oligonucleotides to the $A_1$ and $A_3$ receptors are shown to be effective in the downregulation of $A_1$ or $A_3$ in the cell. One novel feature of this treatment, as compared to traditional treatments for adenosine-mediated bronchoconstriction, is its direct administration to the lungs. The present treatment additionally selectively reduces the amount or level of a receptor protein itself, rather than as is the case with treatments where the agent merely interacts with the receptor. The selective characteristic of the present antisense oligonucleotide results in a reduction in toxicity.

As used herein, the term "treat" or "treating" asthma refers to a treatment which decreases the likelihood that the subject administered such treatment will manifest symptoms of bronchoconstriction or asthma. The term "downregulate", thus, refers to inducing a decrease in production, secretion or availability, and thus a decrease in concentration, of intracellular $A_1$ or $A_3$ adenosine receptor.

The present invention is concerned primarily with the treatment of human subjects but may also be employed for the treatment of other mammalian subjects, such as dogs and cats, for veterinary purposes.

In general, "antisense" refers to the use of small, synthetic oligonucleotides, resembling single-stranded DNA, to inhibit gene expression by inhibiting the function of the target messenger RNA (mRNA). Milligan, J. F. et al., *J. Med. Chem.* 36(14), 1923–1937 (1993). The present invention, thus, is intended for inhibition of gene expression of the $A_1$ or $A_3$ adenosine receptor is desired. Gene expression is inhibited through oligonucleotide hybridization to coding (sense) sequences in a specific messenger RNA (mRNA) target by hydrogen bonding according to Watson-Crick base pairing rules. The mechanism of antisense inhibition is that the exogenously applied oligonucleotides decrease the mRNA and protein levels of the target gene or cause changes in the growth characteristics or shapes of the cells. Id. See also Helene, C. and Toulme, J., *Biochim. Biophys. Acta* 1049, 99–125 (1990); Cohen, J. S., Ed., *Oligodeoxynucleotides as Antisense Inhibitors of Gene Expression*; CRC Press:Boca Raton, Fla. (1987).

As used herein, "adenosine receptor antisense oligonucleotide" is defined as a short sequence of synthetic nucleotides that (1) hybridizes to any coding sequence in an mRNA which codes for the $A_1$ adenosine receptor or $A_3$ adenosine receptor, according to hybridization conditions described below, and (2) upon hybridization causes a decrease in gene expression of the $A_1$ or $A_3$ adenosine receptor.

The mRNA sequence of the $A_1$ or $A_3$ adenosine receptor is derived from the DNA base sequence of the gene expressing either the $A_1$ or $A_3$ adenosine receptor. The sequence of the genomic human $A_1$ adenosine receptor is known and is disclosed in U.S. Pat. No. 5,320,962 to G. Stiles et al. The $A_3$ adenosine receptor has been cloned, sequenced and expressed in rat (see F. Zhou et al., *Proc. Nat'l Acad. Sci. USA* 89:7432 (1992)) and humans (see M. A. Jacobson et al., U.K. Patent Application No. 9304582.1 (1993)). The antisense oligonucleotides that downregulate the production of the $A_1$ or $A_3$ adenosine receptor may be produced in accordance with standard techniques.

The antisense olignucleotide of this invention binds specifically with any sequence of an mRNA molecule which encodes a human $A_1$ adenosine receptor or $A_3$-adenosine receptor and prevents translation of the mRNA molecule. In one embodiment of the present invention, the antisense oligonucleotide has a sequence identified as SEQ ID NO:1, SEQ ID NO:3, and SEQ ID NO:5, shown below.

5'-GAT GGA GGG CGG CAT GGC GGG-3' (SEQ ID NO:1)

5'-GTT GTT GGG CAT CTT GCC-3' (SEQ ID NO:3)

5'-GTG GGC CTA GCT CTC GCC-3' (SEQ ID NO:5)

In another embodiment of the invention, the sequence of the antisense oligonucleotide brackets the initiation codon of the human adenosine $A_1$ receptor. Such an antisense oligonucleotide may have a sequence dislosed herein as follows:

| Sequence | SEQ ID |
|---|---|
| 5'-GGC GGC CTG GAA AGC TGA GAT GGA GGG CGG CAT GGC GGG CAC AGG CTG GGC-3' | (SEQ ID NO:7) |
| 5'-GGC GGC CTG GAA AGC TGA GAT GGA GGG CGG CAT GGC GGG CAC AGG CTG GG-3' | (SEQ ID NO:8) |
| 5'-GGC GGC CTG GAA AGC TGA GAT GGA GGG CGG CAT GGC GGG CAC AGG CTG G-3' | (SEQ ID NO:9) |
| 5'-GGC GGC CTG GAA AGC TGA GAT GGA GGG CGG CAT GGC GGG CAC AGG CTG-3' | (SEQ ID NO:10) |
| 5'-GGC GGC CTG GAA AGC TGA GAT GGA GGG CGG CAT GGC GGG CAC AGG CT-3' | (SEQ ID NO:11) |
| 5'-GGC GGC CTG GAA AGC TGA GAT GGA GGG CGG CAT GGC GGG CAC AGG C-3' | (SEQ ID NO:12) |
| 5'-GGC GGC CTG GAA AGC TGA GAT GGA GGG CGG CAT GGC GGG CAC AGG-3' | (SEQ ID NO:13) |
| 5'-GGC GGC CTG GAA AGC TGA GAT GGA GGG CGG CAT GGC GGG CAC AG-3' | (SEQ ID NO:14) |
| 5'-GGC GGC CTG GAA AGC TGA GAT GGA GGG CGG CAT GGC GGG CAC A-3' | (SEQ ID NO:15) |

-continued

5'-GGC GGC CTG GAA AGC TGA GAT GGA GGG CGG CAT GGC GGG CAC-3' (SEQ ID NO:16)

5'-GGC GGC CTG GAA AGC TGA GAT GGA GGG CGG CAT GGC GGG CA-3' (SEQ ID NO:17)

5'-GGC GGC CTG GAA AGC TGA GAT GGA GGG CGG CAT GGC GGG C-3' (SEQ ID NO:18)

5'-GGC GGC CTG GAA AGC TGA GAT GGA GGG CGG CAT GGC GGG-3' (SEQ ID NO:19)

5'-GGC GGC CTG GAA AGC TGA GAT GGA GGG CGG CAT GGC GG-3' (SEQ ID NO:20)

5'-GGC GGC CTG GAA AGC TGA GAT GGA GGG CGG CAT GGC G-3' (SEQ ID NO:21)

5'-GGC GGC CTG GAA AGC TGA GAT GGA GGG CGG CAT GGC-3' (SEQ ID NO:22)

5'-GGC GGC CTG GAA AGC TGA GAT GGA GGG CGG CAT GG-3' (SEQ ID NO:23)

5'-GGC GGC CTG GAA AGC TGA GAT GGA GGG CGG CAT G-3' (SEQ ID NO:24)

5'-GGC GGC CTG GAA AGC TGA GAT GGA GGG CGG CAT-3' (SEQ ID NO:25)

5'-GGC GGC CTG GAA AGC TGA GAT GGA GGG CGG CA-3' (SEQ ID NO:26)

5'-GGC GGC CTG GAA AGC TGA GAT GGA GGG CGG C-3' (SEQ ID NO:27)

5'-GGC GGC CTG GAA AGC TGA GAT GGA GGG CGG-3' (SEQ ID NO:28)

5'-GGC GGC CTG GAA AGC TGA GAT GGA GGG CG-3' (SEQ ID NO:29)

5'-GGC GGC CTG GAA AGC TGA GAT GGA GGG C-3' (SEQ ID NO:30)

5'-GGC GGC CTG GAA AGC TGA GAT GGA GGG-3' (SEQ ID NO:31)

5'-GGC GGC CTG GAA AGC TGA GAT GGA GG-3' (SEQ ID NO:32)

5'-GGC GGC CTG GAA AGC TGA GAT GGA G-3' (SEQ ID NO:33)

5'-GGC GGC CTG GAA AGC TGA GAT GGA-3' (SEQ ID NO:34)

5'-GGC GGC CTG GAA AGC TGA GAT GG-3' (SEQ ID NO:35)

5'-GGC GGC CTG GAA AGC TGA GAT G-3' (SEQ ID NO:36)

5'-GGC GGC CTG GAA AGC TGA GAT-3' (SEQ ID NO:37)

5'-GGC GGC CTG GAA AGC TGA GA-3' (SEQ ID NO:38)

5'-GGC GGC CTG GAA AGC TGA G-3' (SEQ ID NO:39)

5'-GGC GGC CTG GAA AGC TGA-3' (SEQ ID NO:40)

5'-GGC GGC CTG GAA AGC TG-3' (SEQ ID NO:41)

5'-GGC GGC CTG GAA AGC T-3' (SEQ ID NO:42)

5'-GGC GGC CTG GAA AGC-3' (SEQ ID NO:43)

-continued

| | |
|---|---|
| 5'-GGC GGC CTG GAA AG-3' | (SEQ ID NO:44) |
| 5'-GGC GGC CTG GAA A-3' | (SEQ ID NO:45) |
| 5'-GGC GGC CTG GAA-3' | (SEQ ID NO:46) |
| 5'-GGC GGC CTG GA-3' | (SEQ ID NO:47) |
| 5'-GGC GGC CTG G-3' | (SEQ ID NO:48) |
| 5'-GC GGC CTG GAA AGC TGA GAT GGA GGG CGG CAT GGC GGG CAC AGG CTG GGC-3' | (SEQ ID NO:49) |
| 5'-GC GGC CTG GAA AGC TGA GAT GGA GGG CGG CAT GGC GGG CAC AGG CTG GG-3' | (SEQ ID NO:50) |
| 5'-GC GGC CTG GAA AGC TGA GAT GGA GGG CGG CAT GGC GGG CAC AGG CTG G-3' | (SEQ ID NO:51) |
| 5'-GC GGC CTG GAA AGC TGA GAT GGA GGG CGG CAT GGC GGG CAC AGG CTG-3' | (SEQ ID NO:52) |
| 5'-GC GGC CTG GAA AGC TGA GAT GGA GGG CGG CAT GGC GGG CAC AGG CT-3' | (SEQ ID NO:53) |
| 5'-GC GGC CTG GAA AGC TGA GAT GGA GGG CGG CAT GGC GGG CAC AGG C-3' | (SEQ ID NO:54) |
| 5'-GC GGC CTG GAA AGC TGA GAT GGA GGG CGG CAT GGC GGG CAC AGG-3' | (SEQ ID NO:55) |
| 5'-GC GGC CTG GAA AGC TGA GAT GGA GGG CGG CAT GGC GGG CAC AG-3' | (SEQ ID NO:56) |
| 5'-GC GGC CTG GAA AGC TGA GAT GGA GGG CGG CAT GGC GGG CAC A-3' | (SEQ ID NO:57) |
| 5'-GC GGC CTG GAA AGC TGA GAT GGA GGG CGG CAT GGC GGG CAC-3' | (SEQ ID NO:58) |
| 5'-GC GGC CTG GAA AGC TGA GAT GGA GGG CGG CAT GGC GGG CA-3' | (SEQ ID NO:59) |
| 5'-GC GGC CTG GAA AGC TGA GAT GGA GGG CGG CAT GGC GGG C-3' | (SEQ ID NO:60) |
| 5'-GC GGC CTG GAA AGC TGA GAT GGA GGG CGG CAT GGC GGG-3' | (SEQ ID NO:61) |
| 5'-GC GGC CTG GAA AGC TGA GAT GGA GGG CGG CAT GGC GG-3' | (SEQ ID NO:62) |
| 5'-GC GGC CTG GAA AGC TGA GAT GGA GGG CGG CAT GGC G-3' | (SEQ ID NO:63) |
| 5'-GC GGC CTG GAA AGC TGA GAT GGA GGG CGG CAT GGC-3' | (SEQ ID NO:64) |
| 5'-GC GGC CTG GAA AGC TGA GAT GGA GGG CGG CAT GG-3' | (SEQ ID NO:65) |
| 5'-GC GGC CTG GAA AGC TGA GAT GGA GGG CGG CAT G-3' | (SEQ ID NO:66) |
| 5'-GC GGC CTG GAA AGC TGA GAT GGA GGG CGG CAT-3' | (SEQ ID NO:67) |
| 5'-GC GGC CTG GAA AGC TGA GAT GGA GGG CGG CA-3' | (SEQ ID NO:68) |
| 5'-GC GGC CTG GAA AGC TGA GAT GGA GGG CGG C-3' | (SEQ ID NO:69) |
| 5'-GC GGC CTG GAA AGC TGA GAT GGA GGG CGG-3' | (SEQ ID NO:70) |
| 5'-GC GGC CTG GAA AGC TGA GAT GGA GGG CG-3' | (SEQ ID NO:71) |

-continued

| | |
|---|---|
| 5'-GC GGC CTG GAA AGC TGA GAT GGA GGG C-3' | (SEQ ID NO:72) |
| 5'-GC GGC CTG GAA AGC TGA GAT GGA GGG-3' | (SEQ ID NO:73) |
| 5'-GC GGC CTG GAA AGC TGA GAT GGA GG-3' | (SEQ ID NO:74) |
| 5'-GC GGC CTG GAA AGC TGA GAT GGA G-3' | (SEQ ID NO:75) |
| 5'-GC GGC CTG GAA AGC TGA GAT GGA-3' | (SEQ ID NO:76) |
| 5'-GC GGC CTG GAA AGC TGA GAT GG-3' | (SEQ ID NO:77) |
| 5'-GC GGC CTG GAA AGC TGA GAT G-3' | (SEQ ID NO:78) |
| 5'-GC GGC CTG GAA AGC TGA GAT-3' | (SEQ ID NO:79) |
| 5'-GC GGC CTG GAA AGC TGA GA-3' | (SEQ ID NO:80) |
| 5'-GC GGC CTG GAA AGC TGA G-3' | (SEQ ID NO:81) |
| 5'-GC GGC CTG GAA AGC TGA-3' | (SEQ ID NO:82) |
| 5'-GC GGC CTG GAA AGC TG-3' | (SEQ ID NO:83) |
| 5'-GC GGC CTG GAA AGC T-3' | (SEQ ID NO:84) |
| 5'-GC GGC CTG GAA AGC-3' | (SEQ ID NO:85) |
| 5'-GC GGC CTG GAA AG-3' | (SEQ ID NO:86) |
| 5'-GC GGC CTG GAA A-3' | (SEQ ID NO:87) |
| 5'-GC GGC CTG GAA-3' | (SEQ ID NO:88) |
| 5'-GC GGC CTG GA-3' | (SEQ ID NO:89) |
| 5'-C GGC CTG GAA AGC TGA GAT GGA GGG CGG CAT GGC GGG CAC AGG CTG GGC-3' | (SEQ ID NO:90) |
| 5'-C GGC CTG GAA AGC TGA GAT GGA GGG CGG CAT GGC GGG CAC AGG CTG GG-3' | (SEQ ID NO:91) |
| 5'-C GGC CTG GAA AGC TGA GAT GGA GGG CGG CAT GGC GGG CAC AGG CTG G-3' | (SEQ ID NO:92) |
| 5'-C GGC CTG GAA AGC TGA GAT GGA GGG CGG CAT GGC GGG CAC AGG CTG-3' | (SEQ ID NO:93) |
| 5'-C GGC CTG GAA AGC TGA GAT GGA GGG CGG CAT GGC GGG CAC AGG CT-3' | (SEQ ID NO:94) |
| 5'-C GGC CTG GAA AGC TGA GAT GGA GGG CGG CAT GGC GGG CAC AGG C-3' | (SEQ ID NO:95) |
| 5'-C GGC CTG GAA AGC TGA GAT GGA GGG CGG CAT GGC GGG CAC AGG-3' | (SEQ ID NO:96) |
| 5'-C GGC CTG GAA AGC TGA GAT GGA GGG CGG CAT GGC GGG CAC AG-3' | (SEQ ID NO:97) |
| 5'-C GGC CTG GAA AGC TGA GAT GGA GGG CGG CAT GGC GGG CAC A-3' | (SEQ ID NO:98) |
| 5'-C GGC CTG GAA AGC TGA GAT GGA GGG CGG CAT GGC GGG CAC-3' | (SEQ ID NO:99) |

-continued

5'-C GGC CTG AAA AGC TGA GAT GGA GGG CGG CAT GGC GGG CA-3'  (SEQ ID NO:100)

5'-C GGC CTG AAA AGC TGA GAT GGA GGG CGG CAT GGC GGG C-3'  (SEQ ID NO:101)

5'-C GGC CTG AAA AGC TGA GAT GGA GGG CGG CAT GGC GGG-3'  (SEQ ID NO:102)

5'-C GGC CTG AAA AGC TGA GAT GGA GGG CGG CAT GGC GG-3'  (SEQ ID NO:103)

5'-C GGC CTG AAA AGC TGA GAT GGA GGG CGG CAT GGC G-3'  (SEQ ID NO:104)

5'-C GGC CTG AAA AGC TGA GAT GGA GGG CGG CAT GGC-3'  (SEQ ID NO:105)

5'-C GGC CTG AAA AGC TGA GAT GGA GGG CGG CAT GG-3'  (SEQ ID NO:106)

5'-C GGC CTG AAA AGC TGA GAT GGA GGG CGG CAT G-3'  (SEQ ID NO:107)

5'-C GGC CTG AAA AGC TGA GAT GGA GGG CGG CAT-3'  (SEQ ID NO:108)

5'-C GGC CTG AAA AGC TGA GAT GGA GGG CGG CA-3'  (SEQ ID NO:109)

5'-C GGC CTG AAA AGC TGA GAT GGA GGG CGG C-3'  (SEQ ID NO:110)

5'-C GGC CTG AAA AGC TGA GAT GGA GGG CGG-3'  (SEQ ID NO:111)

5'-C GGC CTG AAA AGC TGA GAT GGA GGG CG-3'  (SEQ ID NO:112)

5'-C GGC CTG AAA AGC TGA GAT GGA GGG C-3'  (SEQ ID NO:113)

5'-C GGC CTG AAA AGC TGA GAT GGA GGG-3'  (SEQ ID NO:114)

5'-C GGC CTG AAA AGC TGA GAT GGA GG-3'  (SEQ ID NO:115)

5'-C GGC CTG AAA AGC TGA GAT GGA G-3'  (SEQ ID NO:116)

5'-C GGC CTG AAA AGC TGA GAT GGA-3'  (SEQ ID NO:117)

5'-C GGC CTG AAA AGC TGA GAT GG-3'  (SEQ ID NO:118)

5'-C GGC CTG AAA AGC TGA GAT G-3'  (SEQ ID NO:119)

5'-C GGC CTG AAA AGC TGA GAT-3'  (SEQ ID NO:120)

5'-C GGC CTG AAA AGC TGA GA-3'  (SEQ ID NO:121)

5'-C GGC CTG AAA AGC TGA G-3'  (SEQ ID NO:122)

5'-C GGC CTG AAA AGC TGA-3'  (SEQ ID NO:123)

5'-C GGC CTG AAA AGC TG-3'  (SEQ ID NO:124)

5'-C GGC CTG AAA AGC T-3'  (SEQ ID NO:125)

5'-C GGC CTG AAA AGC-3'  (SEQ ID NO:126)

5'-C GGC CTG AAA AG-3'  (SEQ ID NO:127)

-continued

| | |
|---|---|
| 5'-C GGC CTG GAA A-3' | (SEQ ID NO:128) |
| 5'-C GGC CTG GAA-3' | (SEQ ID NO:129) |
| 5'-GGC CTG GAA AGC TGA GAT GGA GGG CGG CAT GGC GGG CAC AGG CTG GGC-3' | (SEQ ID NO:130) |
| 5'-GGC CTG GAA AGC TGA GAT GGA GGG CGG CAT GGC GGG CAC AGG CTG GG-3' | (SEQ ID NO:131) |
| 5'-GGC CTG GAA AGC TGA GAT GGA GGG CGG CAT GGC GGG CAC AGG CTG G-3' | (SEQ ID NO:132) |
| 5'-GGC CTG GAA AGC TGA GAT GGA GGG CGG CAT GGC GGG CAC AGG CTG-3' | (SEQ ID NO:133) |
| 5'-GGC CTG GAA AGC TGA GAT GGA GGG CGG CAT GGC GGG CAC AGG CT-3' | (SEQ ID NO:134) |
| 5'-GGC CTG GAA AGC TGA GAT GGA GGG CGG CAT GGC GGG CAC AGG C-3' | (SEQ ID NO:135) |
| 5'-GGC CTG GAA AGC TGA GAT GGA GGG CGG CAT GGC GGG CAC AGG-3' | (SEQ ID NO:136) |
| 5'-GGC CTG GAA AGC TGA GAT GGA GGG CGG CAT GGC GGG CAC AG-3' | (SEQ ID NO:137) |
| 5'-GGC CTG GAA AGC TGA GAT GGA GGG CGG CAT GGC GGG CAC A-3' | (SEQ ID NO:138) |
| 5'-GGC CTG GAA AGC TGA GAT GGA GGG CGG CAT GGC GGG CAC-3' | (SEQ ID NO:139) |
| 5'-GGC CTG GAA AGC TGA GAT GGA GGG CGG CAT GGC GGG CA-3' | (SEQ ID NO:140) |
| 5'-GGC CTG GAA AGC TGA GAT GGA GGG CGG CAT GGC GGG C-3' | (SEQ ID NO:141) |
| 5'-GGC CTG GAA AGC TGA GAT GGA GGG CGG CAT GGC GGG-3' | (SEQ ID NO:142) |
| 5'-GGC CTG GAA AGC TGA GAT GGA GGG CGG CAT GGC GG-3' | (SEQ ID NO:143) |
| 5'-GGC CTG GAA AGC TGA GAT GGA GGG CGG CAT GGC G-3' | (SEQ ID NO:144) |
| 5'-GGC CTG GAA AGC TGA GAT GGA GGG CGG CAT GGC-3' | (SEQ ID NO:145) |
| 5'-GGC CTG GAA AGC TGA GAT GGA GGG CGG CAT GG-3' | (SEQ ID NO:146) |
| 5'-GGC CTG GAA AGC TGA GAT GGA GGG CGG CAT G-3' | (SEQ ID NO:147) |
| 5'-GGC CTG GAA AGC TGA GAT GGA GGG CGG CAT-3' | (SEQ ID NO:148) |
| 5'-GGC CTG GAA AGC TGA GAT GGA GGG CGG CA-3' | (SEQ ID NO:149) |
| 5'-GGC CTG GAA AGC TGA GAT GGA GGG CGG C-3' | (SEQ ID NO:150) |
| 5'-GGC CTG GAA AGC TGA GAT GGA GGG CGG-3' | (SEQ ID NO:151) |
| 5'-GGC CTG GAA AGC TGA GAT GGA GGG CG-3' | (SEQ ID NO:152) |
| 5'-GGC CTG GAA AGC TGA GAT GGA GGG C-3' | (SEQ ID NO:153) |
| 5'-GGC CTG GAA AGC TGA GAT GGA GGG-3' | (SEQ ID NO:154) |
| 5'-GGC CTG GAA AGC TGA GAT GGA GG-3' | (SEQ ID NO:155) |

-continued

| | |
|---|---|
| 5'-GGC CTG AAA AGC TGA GAT GGA G-3' | (SEQ ID NO:156) |
| 5'-GGC CTG AAA AGC TGA GAT GGA-3' | (SEQ ID NO:157) |
| 5'-GGC CTG AAA AGC TGA GAT GG-3' | (SEQ ID NO:158) |
| 5'-GGC CTG AAA AGC TGA GAT G-3' | (SEQ ID NO:159) |
| 5'-GGC CTG AAA AGC TGA GAT-3' | (SEQ ID NO:160) |
| 5'-GGC CTG AAA AGC TGA GA-3' | (SEQ ID NO:161) |
| 5'-GGC CTG AAA AGC TGA G-3' | (SEQ ID NO:162) |
| 5'-GGC CTG AAA AGC TGA-3' | (SEQ ID NO:163) |
| 5'-GGC CTG AAA AGC TG-3' | (SEQ ID NO:164) |
| 5'-GGC CTG AAA AGC T-3' | (SEQ ID NO:165) |
| 5'-GGC CTG AAA AGC-3' | (SEQ ID NO:166) |
| 5'-GGC CTG AAA AG-3' | (SEQ ID NO:167) |
| 5'-GGC CTG AAA A-3' | (SEQ ID NO:168) |
| 5'-GC CTG AAA AGC TGA GAT GGA GGG CGG CAT GGC GGG CAC AGG CTG GGC-3' | (SEQ ID NO:169) |
| 5'-GC CTG AAA AGC TGA GAT GGA GGG CGG CAT GGC GGG CAC AGG CTG GG-3' | (SEQ ID NO:170) |
| 5'-GC CTG AAA AGC TGA GAT GGA GGG CGG CAT GGC GGG CAC AGG CTG G-3' | (SEQ ID NO:171) |
| 5'-GC CTG AAA AGC TGA GAT GGA GGG CGG CAT GGC GGG CAC AGG CTG-3' | (SEQ ID NO:172) |
| 5'-GC CTG AAA AGC TGA GAT GGA GGG CGG CAT GGC GGG CAC AGG CT-3' | (SEQ ID NO:173) |
| 5'-GC CTG AAA AGC TGA GAT GGA GGG CGG CAT GGC GGG CAC AGG C-3' | (SEQ ID NO:174) |
| 5'-GC CTG AAA AGC TGA GAT GGA GGG CGG CAT GGC GGG CAC AGG-3' | (SEQ ID NO:175) |
| 5'-GC CTG AAA AGC TGA GAT GGA GGG CGG CAT GGC GGG CAC AG-3' | (SEQ ID NO:176) |
| 5'-GC CTG AAA AGC TGA GAT GGA GGG CGG CAT GGC GGG CAC A-3' | (SEQ ID NO:177) |
| 5'-GC CTG AAA AGC TGA GAT GGA GGG CGG CAT GGC GGG CAC-3' | (SEQ ID NO:178) |
| 5'-GC CTG AAA AGC TGA GAT GGA GGG CGG CAT GGC GGG CA-3' | (SEQ ID NO:179) |
| 5'-GC CTG AAA AGC TGA GAT GGA GGG CGG CAT GGC GGG C-3' | (SEQ ID NO:180) |
| 5'-GC CTG AAA AGC TGA GAT GGA GGG CGG CAT GGC GGG-3' | (SEQ ID NO:181) |
| 5'-GC CTG AAA AGC TGA GAT GGA GGG CGG CAT GGC GG-3' | (SEQ ID NO:182) |
| 5'-GC CTG AAA AGC TGA GAT GGA GGG CGG CAT GGC G-3' | (SEQ ID NO:183) |

-continued

| | |
|---|---|
| 5'-GC CTG GAA AGC TGA GAT GGA GGG CGG CAT GGC-3' | (SEQ ID NO:184) |
| 5'-GC CTG GAA AGC TGA GAT GGA GGG CGG CAT GG-3' | (SEQ ID NO:185) |
| 5'-GC CTG GAA AGC TGA GAT GGA GGG CGG CAT G-3' | (SEQ ID NO:186) |
| 5'-GC CTG GAA AGC TGA GAT GGA GGG CGG CAT -3' | (SEQ ID NO:187) |
| 5'-GC CTG GAA AGC TGA GAT GGA GGG CGG CA-3' | (SEQ ID NO:188) |
| 5'-GC CTG GAA AGC TGA GAT GGA GGG CGG C-3' | (SEQ ID NO:189) |
| 5'-GC CTG GAA AGC TGA GAT GGA GGG CGG-3' | (SEQ ID NO:190) |
| 5'-GC CTG GAA AGC TGA GAT GGA GGG CG-3' | (SEQ ID NO:191) |
| 5'-GC CTG GAA AGC TGA GAT GGA GGG C-3' | (SEQ ID NO:192) |
| 5'-GC CTG GAA AGC TGA GAT GGA GGG-3' | (SEQ ID NO:193) |
| 5'-GC CTG GAA AGC TGA GAT GGA GG-3' | (SEQ ID NO:194) |
| 5'-GC CTG GAA AGC TGA GAT GGA G-3' | (SEQ ID NO:195) |
| 5'-GC CTG GAA AGC TGA GAT GGA-3' | (SEQ ID NO:196) |
| 5'-GC CTG GAA AGC TGA GAT GG-3' | (SEQ ID NO:197) |
| 5'-GC CTG GAA AGC TGA GAT G-3' | (SEQ ID NO:198) |
| 5'-GC CTG GAA AGC TGA GAT-3' | (SEQ ID NO:199) |
| 5'-GC CTG GAA AGC TGA GA-3' | (SEQ ID NO:200) |
| 5'-GC CTG GAA AGC TGA G-3' | (SEQ ID NO:201) |
| 5'-GC CTG GAA AGC TGA-3' | (SEQ ID NO:202) |
| 5'-GC CTG GAA AGC TG-3' | (SEQ ID NO:203) |
| 5'-GC CTG GAA AGC T-3' | (SEQ ID NO:204) |
| 5'-GC CTG GAA AGC-3' | (SEQ ID NO:205) |
| 5'-GC CTG GAA AG-3' | (SEQ ID NO:206) |
| 5'-C CTG GAA AGC TGA GAT GGA GGG CGG CAT GGC GGG CAC AGG CTG GGC-3' | (SEQ ID NO:207) |
| 5'-C CTG GAA AGC TGA GAT GGA GGG CGG CAT GGC GGG CAC AGG CTG GG-3' | (SEQ ID NO:208) |
| 5'-C CTG GAA AGC TGA GAT GGA GGG CGG CAT GGC GGG CAC AGG CTG G-3' | (SEQ ID NO:209) |
| 5'-C CTG GAA AGC TGA GAT GGA GGG CGG CAT GGC GGG CAC AGG CTG-3' | (SEQ ID NO:210) |
| 5'-C CTG GAA AGC TGA GAT GGA GGG CGG CAT GGC GGG CAC AGG CT-3' | (SEQ ID NO:211) |

-continued

| | |
|---|---|
| 5'-C CTG GAA AGC TGA GAT GGA GGG CGG CAT GGC GGG CAC AGG C-3' | (SEQ ID NO:212) |
| 5'-C CTG GAA AGC TGA GAT GGA GGG CGG CAT GGC GGG CAC AGG-3' | (SEQ ID NO:213) |
| 5'-C CTG GAA AGC TGA GAT GGA GGG CGG CAT GGC GGG CAC AG-3' | (SEQ ID NO:214) |
| 5'-C CTG GAA AGC TGA GAT GGA GGG CGG CAT GGC GGG CAC A-3' | (SEQ ID NO:215) |
| 5'-C CTG GAA AGC TGA GAT GGA GGG CGG CAT GGC GGG CAC-3' | (SEQ ID NO:216) |
| 5'-C CTG GAA AGC TGA GAT GGA GGG CGG CAT GGC GGG CA-3' | (SEQ ID NO:217) |
| 5'-C CTG GAA AGC TGA GAT GGA GGG CGG CAT GGC GGG C-3' | (SEQ ID NO:218) |
| 5'-C CTG GAA AGC TGA GAT GGA GGG CGG CAT GGC GGG-3' | (SEQ ID NO:219) |
| 5'-C CTG GAA AGC TGA GAT GGA GGG CGG CAT GGC GG-3' | (SEQ ID NO:220) |
| 5'-C CTG GAA AGC TGA GAT GGA GGG CGG CAT GGC G-3' | (SEQ ID NO:221) |
| 5'-C CTG GAA AGC TGA GAT GGA GGG CGG CAT GGC-3' | (SEQ ID NO:222) |
| 5'-C CTG GAA AGC TGA GAT GGA GGG CGG CAT GG-3' | (SEQ ID NO:223) |
| 5'-C CTG GAA AGC TGA GAT GGA GGG CGG CAT G-3' | (SEQ ID NO:224) |
| 5'-C CTG GAA AGC TGA GAT GGA GGG CGG CAT-3' | (SEQ ID NO:225) |
| 5'-C CTG GAA AGC TGA GAT GGA GGG CGG CA-3' | (SEQ ID NO:226) |
| 5'-C CTG GAA AGC TGA GAT GGA GGG CGG C-3' | (SEQ ID NO:227) |
| 5'-C CTG GAA AGC TGA GAT GGA GGG CGG-3' | (SEQ ID NO:228) |
| 5'-C CTG GAA AGC TGA GAT GGA GGG CG-3' | (SEQ ID NO:229) |
| 5'-C CTG GAA AGC TGA GAT GGA GGG C-3' | (SEQ ID NO:230) |
| 5'-C CTG GAA AGC TGA GAT GGA GGG -3' | (SEQ ID NO:231) |
| 5'-C CTG GAA AGC TGA GAT GGA GG-3' | (SEQ ID NO:232) |
| 5'-C CTG GAA AGC TGA GAT GGA G-3' | (SEQ ID NO:233) |
| 5'-C CTG GAA AGC TGA GAT GGA-3' | (SEQ ID NO:234) |
| 5'-C CTG GAA AGC TGA GAT GG-3' | (SEQ ID NO:235) |
| 5'-C CTG GAA AGC TGA GAT G-3' | (SEQ ID NO:236) |
| 5'-C CTG GAA AGC TGA GAT-3' | (SEQ ID NO:237) |
| 5'-C CTG GAA AGC TGA GA-3' | (SEQ ID NO:238) |
| 5'-C CTG GAA AGC TGA G-3' | (SEQ ID NO:239) |

-continued

| | |
|---|---|
| 5'-C CTG GAA AGC TGA-3' | (SEQ ID NO:240) |
| 5'-C CTG GAA AGC TG-3' | (SEQ ID NO:241) |
| 5'-C CTG GAA AGC T-3' | (SEQ ID NO:242) |
| 5'-C CTG GAA AGC-3' | (SEQ ID NO:243) |
| 5'-CTG GAA AGC TGA GAT GGA GGG CGG CAT GGC GGG CAC AGG CTG GGC-3' | (SEQ ID NO:244) |
| 5'-CTG GAA AGC TGA GAT GGA GGG CGG CAT GGC GGG CAC AGG CTG GG-3' | (SEQ ID NO:245) |
| 5'-CTG GAA AGC TGA GAT GGA GGG CGG CAT GGC GGG CAC AGG CTG G-3' | (SEQ ID NO:246) |
| 5'-CTG GAA AGC TGA GAT GGA GGG CGG CAT GGC GGG CAC AGG CTG-3' | (SEQ ID NO:247) |
| 5'-CTG GAA AGC TGA GAT GGA GGG CGG CAT GGC GGG CAC AGG CT-3' | (SEQ ID NO:248) |
| 5'-CTG GAA AGC TGA GAT GGA GGG CGG CAT GGC GGG CAC AGG C-3' | (SEQ ID NO:249) |
| 5'-CTG GAA AGC TGA GAT GGA GGG CGG CAT GGC GGG CAC AGG-3' | (SEQ ID NO:250) |
| 5'-CTG GAA AGC TGA GAT GGA GGG CGG CAT GGC GGG CAC AG-3' | (SEQ ID NO:251) |
| 5'-CTG GAA AGC TGA GAT GGA GGG CGG CAT GGC GGG CAC A-3' | (SEQ ID NO:252) |
| 5'-CTG GAA AGC TGA GAT GGA GGG CGG CAT GGC GGG CAC-3' | (SEQ ID NO:253) |
| 5'-CTG GAA AGC TGA GAT GGA GGG CGG CAT GGC GGG CA-3' | (SEQ ID NO:254) |
| 5'-CTG GAA AGC TGA GAT GGA GGG CGG CAT GGC GGG C-3' | (SEQ ID NO:255) |
| 5'-CTG GAA AGC TGA GAT GGA GGG CGG CAT GGC GGG-3' | (SEQ ID NO:256) |
| 5'-CTG GAA AGC TGA GAT GGA GGG CGG CAT GGC GG-3' | (SEQ ID NO:257) |
| 5'-CTG GAA AGC TGA GAT GGA GGG CGG CAT GGC G-3' | (SEQ ID NO:258) |
| 5'-CTG GAA AGC TGA GAT GGA GGG CGG CAT GGC-3' | (SEQ ID NO:259) |
| 5'-CTG GAA AGC TGA GAT GGA GGG CGG CAT GG-3' | (SEQ ID NO:260) |
| 5'-CTG GAA AGC TGA GAT GGA GGG CGG CAT G-3' | (SEQ ID NO:261) |
| 5'-CTG GAA AGC TGA GAT GGA GGG CGG CAT-3' | (SEQ ID NO:262) |
| 5'-CTG GAA AGC TGA GAT GGA GGG CGG CA-3' | (SEQ ID NO:263) |
| 5'-CTG GAA AGC TGA GAT GGA GGG CGG C-3' | (SEQ ID NO:264) |
| 5'-CTG GAA AGC TGA GAT GGA GGG CGG-3' | (SEQ ID NO:265) |
| 5'-CTG GAA AGC TGA GAT GGA GGG CG-3' | (SEQ ID NO:266) |
| 5'-CTG GAA AGC TGA GAT GGA GGG C-3' | (SEQ ID NO:267) |

-continued

| | |
|---|---|
| 5'-CTG AAA AGC TGA GAT GGA GGG-3' | (SEQ ID NO:268) |
| 5'-CTG AAA AGC TGA GAT GGA GG-3' | (SEQ ID NO:269) |
| 5'-CTG AAA AGC TGA GAT GGA G-3' | (SEQ ID NO:270) |
| 5'-CTG AAA AGC TGA GAT GGA-3' | (SEQ ID NO:271) |
| 5'-CTG AAA AGC TGA GAT GG-3' | (SEQ ID NO:272) |
| 5'-CTG AAA AGC TGA GAT G-3' | (SEQ ID NO:273) |
| 5'-CTG AAA AGC TGA GAT-3' | (SEQ ID NO:274) |
| 5'-CTG AAA AGC TGA GA-3' | (SEQ ID NO:275) |
| 5'-CTG AAA AGC TGA G-3' | (SEQ ID NO:276) |
| 5'-CTG AAA AGC TGA-3' | (SEQ ID NO:277) |
| 5'-CTG AAA AGC TG-3' | (SEQ ID NO:278) |
| 5'-CTG AAA AGC T-3' | (SEQ ID NO:279) |
| 5'-TG AAA AGC TGA GAT GGA GGG CGG CAT GGC GGG CAC AGG CTG GGC-3' | (SEQ ID NO:280) |
| 5'-TG AAA AGC TGA GAT GGA GGG CGG CAT GGC GGG CAC AGG CTG GG-3' | (SEQ ID NO:281) |
| 5'-TG AAA AGC TGA GAT GGA GGG CGG CAT GGC GGG CAC AGG CTG G-3' | (SEQ ID NO:282) |
| 5'-TG AAA AGC TGA GAT GGA GGG CGG CAT GGC GGG CAC AGG CTG-3' | (SEQ ID NO:283) |
| 5'-TG AAA AGC TGA GAT GGA GGG CGG CAT GGC GGG CAC AGG CT-3' | (SEQ ID NO:284) |
| 5'-TG AAA AGC TGA GAT GGA GGG CGG CAT GGC GGG CAC AGG C-3' | (SEQ ID NO:285) |
| 5'-TG AAA AGC TGA GAT GGA GGG CGG CAT GGC GGG CAC AGG-3' | (SEQ ID NO:286) |
| 5'-TG AAA AGC TGA GAT GGA GGG CGG CAT GGC GGG CAC AG-3' | (SEQ ID NO:287) |
| 5'-TG AAA AGC TGA GAT GGA GGG CGG CAT GGC GGG CAC A-3' | (SEQ ID NO:288) |
| 5'-TG AAA AGC TGA GAT GGA GGG CGG CAT GGC GGG CAC-3' | (SEQ ID NO:289) |
| 5'-TG AAA AGC TGA GAT GGA GGG CGG CAT GGC GGG CA-3' | (SEQ ID NO:290) |
| 5'-TG AAA AGC TGA GAT GGA GGG CGG CAT GGC GGG C-3' | (SEQ ID NO:291) |
| 5'-TG AAA AGC TGA GAT GGA GGG CGG CAT GGC GGG-3' | (SEQ ID NO:292) |
| 5'-TG AAA AGC TGA GAT GGA GGG CGG CAT GGC GG-3' | (SEQ ID NO:293) |
| 5'-TG AAA AGC TGA GAT GGA GGG CGG CAT GGC G-3' | (SEQ ID NO:294) |
| 5'-TG AAA AGC TGA GAT GGA GGG CGG CAT GGC-3' | (SEQ ID NO:295) |

-continued

| | |
|---|---|
| 5'-TG AAA AGC TGA GAT GGA GGG CGG CAT GG-3' | (SEQ ID NO:296) |
| 5'-TG AAA AGC TGA GAT GGA GGG CGG CAT G-3' | (SEQ ID NO:297) |
| 5'-TG AAA AGC TGA GAT GGA GGG CGG CAT-3' | (SEQ ID NO:298) |
| 5'-TG AAA AGC TGA GAT GGA GGG CGG CA-3' | (SEQ ID NO:299) |
| 5'-TG AAA AGC TGA GAT GGA GGG CGG C-3' | (SEQ ID NO:300) |
| 5'-TG AAA AGC TGA GAT GGA GGG CGG-3' | (SEQ ID NO:301) |
| 5'-TG AAA AGC TGA GAT GGA GGG CG-3' | (SEQ ID NO:302) |
| 5'-TG AAA AGC TGA GAT GGA GGG C-3' | (SEQ ID NO:303) |
| 5'-TG AAA AGC TGA GAT GGA GGG-3' | (SEQ ID NO:304) |
| 5'-TG AAA AGC TGA GAT GGA GG-3' | (SEQ ID NO:305) |
| 5'-TG AAA AGC TGA GAT GGA G-3' | (SEQ ID NO:306) |
| 5'-TG AAA AGC TGA GAT GGA-3' | (SEQ ID NO:307) |
| 5'-TG AAA AGC TGA GAT GG-3' | (SEQ ID NO:308) |
| 5'-TG AAA AGC TGA GAT G-3' | (SEQ ID NO:309) |
| 5'-TG AAA AGC TGA GAT-3' | (SEQ ID NO:310) |
| 5'-TG AAA AGC TGA GA-3' | (SEQ ID NO:311) |
| 5'-TG AAA AGC TGA G-3' | (SEQ ID NO:312) |
| 5'-TG AAA AGC TGA-3' | (SEQ ID NO:313) |
| 5'-TG AAA AGC TG-3' | (SEQ ID NO:314) |
| 5'-G AAA AGC TGA GAT GGA GGG CGG CAT GGC GGG CAC AGG CTG GGC-3' | (SEQ ID NO:315) |
| 5'-G AAA AGC TGA GAT GGA GGG CGG CAT GGC GGG CAC AGG CTG GG-3' | (SEQ ID NO:316) |
| 5'-G AAA AGC TGA GAT GGA GGG CGG CAT GGC GGG CAC AGG CTG G-3' | (SEQ ID NO:317) |
| 5'-G AAA AGC TGA GAT GGA GGG CGG CAT GGC GGG CAC AGG CTG-3' | (SEQ ID NO:318) |
| 5'-G AAA AGC TGA GAT GGA GGG CGG CAT GGC GGG CAC AGG CT-3' | (SEQ ID NO:319) |
| 5'-G AAA AGC TGA GAT GGA GGG CGG CAT GGC GGG CAC AGG C-3' | (SEQ ID NO:320) |
| 5'-G AAA AGC TGA GAT GGA GGG CGG CAT GGC GGG CAC AGG-3' | (SEQ ID NO:321) |
| 5'-G AAA AGC TGA GAT GGA GGG CGG CAT GGC GGG CAC AG-3' | (SEQ ID NO:322) |
| 5'-G AAA AGC TGA GAT GGA GGG CGG CAT GGC GGG CAC A-3' | (SEQ ID NO:323) |

-continued

| | |
|---|---|
| 5'-G AAA AGC TGA GAT GGA GGG CGG CAT GGC GGG CAC-3' | (SEQ ID NO:324) |
| 5'-G AAA AGC TGA GAT GGA GGG CGG CAT GGC GGG CA-3' | (SEQ ID NO:325) |
| 5'-G AAA AGC TGA GAT GGA GGG CGG CAT GGC GGG C-3' | (SEQ ID NO:326) |
| 5'-G AAA AGC TGA GAT GGA GGG CGG CAT GGC GGG-3' | (SEQ ID NO:327) |
| 5'-G AAA AGC TGA GAT GGA GGG CGG CAT GGC GG-3' | (SEQ ID NO:328) |
| 5'-G AAA AGC TGA GAT GGA GGG CGG CAT GGC G-3' | (SEQ ID NO:329) |
| 5'-G AAA AGC TGA GAT GGA GGG CGG CAT GGC-3' | (SEQ ID NO:330) |
| 5'-G AAA AGC TGA GAT GGA GGG CGG CAT GG-3' | (SEQ ID NO:331) |
| 5'-G AAA AGC TGA GAT GGA GGG CGG CAT G-3' | (SEQ ID NO:332) |
| 5'-G AAA AGC TGA GAT GGA GGG CGG CAT-3' | (SEQ ID NO:333) |
| 5'-G AAA AGC TGA GAT GGA GGG CGG CA-3' | (SEQ ID NO:334) |
| 5'-G AAA AGC TGA GAT GGA GGG CGG C-3' | (SEQ ID NO:335) |
| 5'-G AAA AGC TGA GAT GGA GGG CGG-3' | (SEQ ID NO:336) |
| 5'-G AAA AGC TGA GAT GGA GGG CG-3' | (SEQ ID NO:337) |
| 5'-G AAA AGC TGA GAT GGA GGG C-3' | (SEQ ID NO:338) |
| 5'-G AAA AGC TGA GAT GGA GGG-3' | (SEQ ID NO:339) |
| 5'-G AAA AGC TGA GAT GGA GG-3' | (SEQ ID NO:340) |
| 5'-G AAA AGC TGA GAT GGA G-3' | (SEQ ID NO:341) |
| 5'-G AAA AGC TGA GAT GGA-3' | (SEQ ID NO:342) |
| 5'-G AAA AGC TGA GAT GG-3' | (SEQ ID NO:343) |
| 5'-G AAA AGC TGA GAT G-3' | (SEQ ID NO:344) |
| 5'-G AAA AGC TGA GAT-3' | (SEQ ID NO:345) |
| 5'-G AAA AGC TGA GA-3' | (SEQ ID NO:346) |
| 5'-G AAA AGC TGA G-3' | (SEQ ID NO:347) |
| 5'-G AAA AGC TGA-3' | (SEQ ID NO:348) |
| 5'-AAA AGC TGA GAT GGA GGG CGG CAT GGC GGG CAC AGG CTG GGC-3' | (SEQ ID NO:349) |
| 5'-AAA AGC TGA GAT GGA GGG CGG CAT GGC GGG CAC AGG CTG GG-3' | (SEQ ID NO:350) |
| 5'-AAA AGC TGA GAT GGA GGG CGG CAT GGC GGG CAC AGG CTG G-3' | (SEQ ID NO:351) |

-continued

5'-GAA AGC TGA GAT GGA GGG CGG CAT GGC GGG CAC AGG CTG-3'  (SEQ ID NO:352)

5'-GAA AGC TGA GAT GGA GGG CGG CAT GGC GGG CAC AGG CT-3'  (SEQ ID NO:353)

5'-GAA AGC TGA GAT GGA GGG CGG CAT GGC GGG CAC AGG C-3'  (SEQ ID NO:354)

5'-GAA AGC TGA GAT GGA GGG CGG CAT GGC GGG CAC AGG-3'  (SEQ ID NO:355)

5'-GAA AGC TGA GAT GGA GGG CGG CAT GGC GGG CAC AG-3'  (SEQ ID NO:356)

5'-GAA AGC TGA GAT GGA GGG CGG CAT GGC GGG CAC A-3'  (SEQ ID NO:357)

5'-GAA AGC TGA GAT GGA GGG CGG CAT GGC GGG CAC-3'  (SEQ ID NO:358)

5'-GAA AGC TGA GAT GGA GGG CGG CAT GGC GGG CA-3'  (SEQ ID NO:359)

5'-GAA AGC TGA GAT GGA GGG CGG CAT GGC GGG C-3'  (SEQ ID NO:360)

5'-GAA AGC TGA GAT GGA GGG CGG CAT GGC GGG-3'  (SEQ ID NO:361)

5'-GAA AGC TGA GAT GGA GGG CGG CAT GGC GG-3'  (SEQ ID NO:362)

5'-GAA AGC TGA GAT GGA GGG CGG CAT GGC G-3'  (SEQ ID NO:363)

5'-GAA AGC TGA GAT GGA GGG CGG CAT GGC-3'  (SEQ ID NO:364)

5'-GAA AGC TGA GAT GGA GGG CGG CAT GG-3'  (SEQ ID NO:365)

5'-GAA AGC TGA GAT GGA GGG CGG CAT G-3'  (SEQ ID NO:366)

5'-GAA AGC TGA GAT GGA GGG CGG CAT-3'  (SEQ ID NO:367)

5'-GAA AGC TGA GAT GGA GGG CGG CA-3'  (SEQ ID NO:368)

5'-GAA AGC TGA GAT GGA GGG CGG C-3'  (SEQ ID NO:369)

5'-GAA AGC TGA GAT GGA GGG CGG-3'  (SEQ ID NO:370)

5'-GAA AGC TGA GAT GGA GGG CG-3'  (SEQ ID NO:371)

5'-GAA AGC TGA GAT GGA GGG C-3'  (SEQ ID NO:372)

5'-GAA AGC TGA GAT GGA GGG-3'  (SEQ ID NO:373)

5'-GAA AGC TGA GAT GGA GG-3'  (SEQ ID NO:374)

5'-GAA AGC TGA GAT GGA G-3'  (SEQ ID NO:375)

5'-GAA AGC TGA GAT GGA-3'  (SEQ ID NO:376)

5'-GAA AGC TGA GAT GG-3'  (SEQ ID NO:377)

5'-GAA AGC TGA GAT G-3'  (SEQ ID NO:378)

5'-GAA AGC TGA GAT-3'  (SEQ ID NO:379)

-continued

5'-GAA AGC TGA GA-3' (SEQ ID NO:380)

5'-GAA AGC TGA G-3' (SEQ ID NO:381)

5'-AA AGC TGA GAT GGA GGG CGG CAT GGC GGG CAC AGG CTG GGC-3' (SEQ ID NO:382)

5'-AA AGC TGA GAT GGA GGG CGG CAT GGC GGG CAC AGG CTG GG-3' (SEQ ID NO:383)

5'-AA AGC TGA GAT GGA GGG CGG CAT GGC GGG CAC AGG CTG G-3' (SEQ ID NO:384)

5'-AA AGC TGA GAT GGA GGG CGG CAT GGC GGG CAC AGG CTG-3' (SEQ ID NO:385)

5'-AA AGC TGA GAT GGA GGG CGG CAT GGC GGG CAC AGG CT-3' (SEQ ID NO:386)

5'-AA AGC TGA GAT GGA GGG CGG CAT GGC GGG CAC AGG C-3' (SEQ ID NO:387)

5'-AA AGC TGA GAT GGA GGG CGG CAT GGC GGG CAC AGG-3' (SEQ ID NO:388)

5'-AA AGC TGA GAT GGA GGG CGG CAT GGC GGG CAC AG-3' (SEQ ID NO:389)

5'-AA AGC TGA GAT GGA GGG CGG CAT GGC GGG CAC A-3' (SEQ ID NO:390)

5'-AA AGC TGA GAT GGA GGG CGG CAT GGC GGG CAC-3' (SEQ ID NO:391)

5'-AA AGC TGA GAT GGA GGG CGG CAT GGC GGG CA-3' (SEQ ID NO:392)

5'-AA AGC TGA GAT GGA GGG CGG CAT GGC GGG C-3' (SEQ ID NO:393)

5'-AA AGC TGA GAT GGA GGG CGG CAT GGC GGG-3' (SEQ ID NO:394)

5'-AA AGC TGA GAT GGA GGG CGG CAT GGC GG-3' (SEQ ID NO:395)

5'-AA AGC TGA GAT GGA GGG CGG CAT GGC G-3' (SEQ ID NO:396)

5'-AA AGC TGA GAT GGA GGG CGG CAT GGC-3' (SEQ ID NO:397)

5'-AA AGC TGA GAT GGA GGG CGG CAT GG-3' (SEQ ID NO:398)

5'-AA AGC TGA GAT GGA GGG CGG CAT G-3' (SEQ ID NO:399)

5'-AA AGC TGA GAT GGA GGG CGG CAT-3' (SEQ ID NO:400)

5'-AA AGC TGA GAT GGA GGG CGG CA-3' (SEQ ID NO:401)

5'-AA AGC TGA GAT GGA GGG CGG C-3' (SEQ ID NO:402)

5'-AA AGC TGA GAT GGA GGG CGG-3' (SEQ ID NO:403)

5'-AA AGC TGA GAT GGA GGG CG-3' (SEQ ID NO:404)

5'-AA AGC TGA GAT GGA GGG C-3' (SEQ ID NO:405)

5'-AA AGC TGA GAT GGA GGG-3' (SEQ ID NO:406)

5'-AA AGC TGA GAT GGA GG-3' (SEQ ID NO:407)

-continued

| | |
|---|---|
| 5'-AA AGC TGA GAT GGA G-3' | (SEQ ID NO:408) |
| 5'-AA AGC TGA GAT GGA-3' | (SEQ ID NO:409) |
| 5'-AA AGC TGA GAT GG-3' | (SEQ ID NO:410) |
| 5'-AA AGC TGA GAT G-3' | (SEQ ID NO:411) |
| 5'-AA AGC TGA GAT-3' | (SEQ ID NO:412) |
| 5'-AA AGC TGA GA-3' | (SEQ ID NO:413) |
| 5'-A AGC TGA GAT GGA GGG CGG CAT GGC GGG CAC AGG CTG GGC-3' | (SEQ ID NO:414) |
| 5'-A AGC TGA GAT GGA GGG CGG CAT GGC GGG CAC AGG CTG GG-3' | (SEQ ID NO:415) |
| 5'-A AGC TGA GAT GGA GGG CGG CAT GGC GGG CAC AGG CTG G-3' | (SEQ ID NO:416) |
| 5'-A AGC TGA GAT GGA GGG CGG CAT GGC GGG CAC AGG CTG-3' | (SEQ ID NO:417) |
| 5'-A AGC TGA GAT GGA GGG CGG CAT GGC GGG CAC AGG CT-3' | (SEQ ID NO:418) |
| 5'-A AGC TGA GAT GGA GGG CGG CAT GGC GGG CAC AGG C-3' | (SEQ ID NO:419) |
| 5'-A AGC TGA GAT GGA GGG CGG CAT GGC GGG CAC AGG-3' | (SEQ ID NO:420) |
| 5'-A AGC TGA GAT GGA GGG CGG CAT GGC GGG CAC AG-3' | (SEQ ID NO:421) |
| 5'-A AGC TGA GAT GGA GGG CGG CAT GGC GGG CAC A-3' | (SEQ ID NO:422) |
| 5'-A AGC TGA GAT GGA GGG CGG CAT GGC GGG CAC-3' | (SEQ ID NO:423) |
| 5'-A AGC TGA GAT GGA GGG CGG CAT GGC GGG CA-3' | (SEQ ID NO:424) |
| 5'-A AGC TGA GAT GGA GGG CGG CAT GGC GGG C-3' | (SEQ ID NO:425) |
| 5'-A AGC TGA GAT GGA GGG CGG CAT GGC GGG-3' | (SEQ ID NO:426) |
| 5'-A AGC TGA GAT GGA GGG CGG CAT GGC GG-3' | (SEQ ID NO:427) |
| 5'-A AGC TGA GAT GGA GGG CGG CAT GGC G-3' | (SEQ ID NO:428) |
| 5'-A AGC TGA GAT GGA GGG CGG CAT GGC-3' | (SEQ ID NO:429) |
| 5'-A AGC TGA GAT GGA GGG CGG CAT GG-3' | (SEQ ID NO:430) |
| 5'-A AGC TGA GAT GGA GGG CGG CAT G-3' | (SEQ ID NO:431) |
| 5'-A AGC TGA GAT GGA GGG CGG CAT-3' | (SEQ ID NO:432) |
| 5'-A AGC TGA GAT GGA GGG CGG CA-3' | (SEQ ID NO:433) |
| 5'-A AGC TGA GAT GGA GGG CGG C-3' | (SEQ ID NO:434) |
| 5'-A AGC TGA GAT GGA GGG CGG-3' | (SEQ ID NO:435) |

-continued

| | |
|---|---|
| 5'-A AGC TGA GAT GGA GGG CG-3' | (SEQ ID NO:436) |
| 5'-A AGC TGA GAT GGA GGG C-3' | (SEQ ID NO:437) |
| 5'-A AGC TGA GAT GGA GGG-3' | (SEQ ID NO:438) |
| 5'-A AGC TGA GAT GGA GG-3' | (SEQ ID NO:439) |
| 5'-A AGC TGA GAT GGA G-3' | (SEQ ID NO:440) |
| 5'-A AGC TGA GAT GGA-3' | (SEQ ID NO:441) |
| 5'-A AGC TGA GAT GG-3' | (SEQ ID NO:442) |
| 5'-A AGC TGA GAT G-3' | (SEQ ID NO:443) |
| 5'-A AGC TGA GAT-3' | (SEQ ID NO:444) |
| 5'-AGC TGA GAT GGA GGG CGG CAT GGC GGG CAC AGG CTG GGC-3' | (SEQ ID NO:445) |
| 5'-AGC TGA GAT GGA GGG CGG CAT GGC GGG CAC AGG CTG GG-3' | (SEQ ID NO:446) |
| 5'-AGC TGA GAT GGA GGG CGG CAT GGC GGG CAC AGG CTG G-3' | (SEQ ID NO:447) |
| 5'-AGC TGA GAT GGA GGG CGG CAT GGC GGG CAC AGG CTG-3' | (SEQ ID NO:448) |
| 5'-AGC TGA GAT GGA GGG CGG CAT GGC GGG CAC AGG CT-3' | (SEQ ID NO:449) |
| 5'-AGC TGA GAT GGA GGG CGG CAT GGC GGG CAC AGG C-3' | (SEQ ID NO:450) |
| 5'-AGC TGA GAT GGA GGG CGG CAT GGC GGG CAC AGG-3' | (SEQ ID NO:451) |
| 5'-AGC TGA GAT GGA GGG CGG CAT GGC GGG CAC AG-3' | (SEQ ID NO:452) |
| 5'-AGC TGA GAT GGA GGG CGG CAT GGC GGG CAC A-3' | (SEQ ID NO:453) |
| 5'-AGC TGA GAT GGA GGG CGG CAT GGC GGG CAC-3' | (SEQ ID NO:454) |
| 5'-AGC TGA GAT GGA GGG CGG CAT GGC GGG CA-3' | (SEQ ID NO:455) |
| 5'-AGC TGA GAT GGA GGG CGG CAT GGC GGG C-3' | (SEQ ID NO:456) |
| 5'-AGC TGA GAT GGA GGG CGG CAT GGC GGG-3' | (SEQ ID NO:457) |
| 5'-AGC TGA GAT GGA GGG CGG CAT GGC GG-3' | (SEQ ID NO:458) |
| 5'-AGC TGA GAT GGA GGG CGG CAT GGC G-3' | (SEQ ID NO:459) |
| 5'-AGC TGA GAT GGA GGG CGG CAT GGC-3' | (SEQ ID NO:460) |
| 5'-AGC TGA GAT GGA GGG CGG CAT GG-3' | (SEQ ID NO:461) |
| 5'-AGC TGA GAT GGA GGG CGG CAT G-3' | (SEQ ID NO:462) |
| 5'-AGC TGA GAT GGA GGG CGG CAT-3' | (SEQ ID NO:463) |

-continued

5'-AGC TGA GAT GGA GGG CGG CA-3' (SEQ ID NO:464)

5'-AGC TGA GAT GGA GGG CGG C-3' (SEQ ID NO:465)

5'-AGC TGA GAT GGA GGG CGG-3' (SEQ ID NO:466)

5'-AGC TGA GAT GGA GGG CG-3' (SEQ ID NO:467)

5'-AGC TGA GAT GGA GGG C-3' (SEQ ID NO:468)

5'-AGC TGA GAT GGA GGG-3' (SEQ ID NO:469)

5'-AGC TGA GAT GGA GG-3' (SEQ ID NO:470)

5'-AGC TGA GAT GGA G-3' (SEQ ID NO:471)

5'-AGC TGA GAT GGA-3' (SEQ ID NO:472)

5'-AGC TGA GAT GG-3' (SEQ ID NO:473)

5'-AGC TGA GAT G-3' (SEQ ID NO:474)

5'-GC TGA GAT GGA GGG CGG CAT GGC GGG CAC AGG CTG GGC-3' (SEQ ID NO:475)

5'-GC TGA GAT GGA GGG CGG CAT GGC GGG CAC AGG CTG GG-3' (SEQ ID NO:476)

5'-GC TGA GAT GGA GGG CGG CAT GGC GGG CAC AGG CTG G-3' (SEQ ID NO:477)

5'-GC TGA GAT GGA GGG CGG CAT GGC GGG CAC AGG CTG-3' (SEQ ID NO:478)

5'-GC TGA GAT GGA GGG CGG CAT GGC GGG CAC AGG CT-3' (SEQ ID NO:479)

5'-GC TGA GAT GGA GGG CGG CAT GGC GGG CAC AGG C-3' (SEQ ID NO:480)

5'-GC TGA GAT GGA GGG CGG CAT GGC GGG CAC AGG-3' (SEQ ID NO:481)

5'-GC TGA GAT GGA GGG CGG CAT GGC GGG CAC AG-3' (SEQ ID NO:482)

5'-GC TGA GAT GGA GGG CGG CAT GGC GGG CAC A-3' (SEQ ID NO:483)

5'-GC TGA GAT GGA GGG CGG CAT GGC GGG CAC-3' (SEQ ID NO:484)

5'-GC TGA GAT GGA GGG CGG CAT GGC GGG CA-3' (SEQ ID NO:485)

5'-GC TGA GAT GGA GGG CGG CAT GGC GGG C-3' (SEQ ID NO:486)

5'-GC TGA GAT GGA GGG CGG CAT GGC GGG-3' (SEQ ID NO:487)

5'-GC TGA GAT GGA GGG CGG CAT GGC GG-3' (SEQ ID NO:488)

5'-GC TGA GAT GGA GGG CGG CAT GGC G-3' (SEQ ID NO:489)

5'-GC TGA GAT GGA GGG CGG CAT GGC-3' (SEQ ID NO:490)

5'-GC TGA GAT GGA GGG CGG CAT GG-3' (SEQ ID NO:491)

-continued

| | |
|---|---|
| 5'-GC TGA GAT GGA GGG CGG CAT G-3' | (SEQ ID NO:492) |
| 5'-GC TGA GAT GGA GGG CGG CAT-3' | (SEQ ID NO:493) |
| 5'-GC TGA GAT GGA GGG CGG CA-3' | (SEQ ID NO:494) |
| 5'-GC TGA GAT GGA GGG CGG C-3' | (SEQ ID NO:495) |
| 5'-GC TGA GAT GGA GGG CGG-3' | (SEQ ID NO:496) |
| 5'-GC TGA GAT GGA GGG CG-3' | (SEQ ID NO:497) |
| 5'-GC TGA GAT GGA GGG C-3' | (SEQ ID NO:498) |
| 5'-GC TGA GAT GGA GGG-3' | (SEQ ID NO:499) |
| 5'-GC TGA GAT GGA GG-3' | (SEQ ID NO:500) |
| 5'-GC TGA GAT GGA G-3' | (SEQ ID NO:501) |
| 5'-GC TGA GAT GGA-3' | (SEQ ID NO:502) |
| 5'-GC TGA GAT GG-3' | (SEQ ID NO:503) |
| 5'-C TGA GAT GGA GGG CGG CAT GGC GGG CAC AGG CTG GGC-3' | (SEQ ID NO:504) |
| 5'-C TGA GAT GGA GGG CGG CAT GGC GGG CAC AGG CTG GG-3' | (SEQ ID NO:505) |
| 5'-C TGA GAT GGA GGG CGG CAT GGC GGG CAC AGG CTG G-3' | (SEQ ID NO:506) |
| 5'-C TGA GAT GGA GGG CGG CAT GGC GGG CAC AGG CTG-3' | (SEQ ID NO:507) |
| 5'-C TGA GAT GGA GGG CGG CAT GGC GGG CAC AGG CT-3' | (SEQ ID NO:508) |
| 5'-C TGA GAT GGA GGG CGG CAT GGC GGG CAC AGG C-3' | (SEQ ID NO:509) |
| 5'-C TGA GAT GGA GGG CGG CAT GGC GGG CAC AGG-3' | (SEQ ID NO:510) |
| 5'-C TGA GAT GGA GGG CGG CAT GGC GGG CAC AG-3' | (SEQ ID NO:511) |
| 5'-C TGA GAT GGA GGG CGG CAT GGC GGG CAC A-3' | (SEQ ID NO:512) |
| 5'-C TGA GAT GGA GGG CGG CAT GGC GGG CAC-3' | (SEQ ID NO:513) |
| 5'-C TGA GAT GGA GGG CGG CAT GGC GGG CA-3' | (SEQ ID NO:514) |
| 5'-C TGA GAT GGA GGG CGG CAT GGC GGG C-3' | (SEQ ID NO:515) |
| 5'-C TGA GAT GGA GGG CGG CAT GGC GGG-3' | (SEQ ID NO:516) |
| 5'-C TGA GAT GGA GGG CGG CAT GGC GG-3' | (SEQ ID NO:517) |
| 5'-C TGA GAT GGA GGG CGG CAT GGC G-3' | (SEQ ID NO:518) |
| 5'-C TGA GAT GGA GGG CGG CAT GGC-3' | (SEQ ID NO:519) |

-continued

| | |
|---|---|
| 5'-C TGA GAT GGA GGG CGG CAT GG-3' | (SEQ ID NO:520) |
| 5'-C TGA GAT GGA GGG CGG CAT G-3' | (SEQ ID NO:521) |
| 5'-C TGA GAT GGA GGG CGG CAT-3' | (SEQ ID NO:522) |
| 5'-C TGA GAT GGA GGG CGG CA-3' | (SEQ ID NO:523) |
| 5'-C TGA GAT GGA GGG CGG C-3' | (SEQ ID NO:524) |
| 5'-C TGA GAT GGA GGG CGG-3' | (SEQ ID NO:525) |
| 5'-C TGA GAT GGA GGG CG-3' | (SEQ ID NO:526) |
| 5'-C TGA GAT GGA GGG C-3' | (SEQ ID NO:527) |
| 5'-C TGA GAT GGA GGG-3' | (SEQ ID NO:528) |
| 5'-C TGA GAT GGA GG-3' | (SEQ ID NO:529) |
| 5'-C TGA GAT GGA G-3' | (SEQ ID NO:530) |
| 5'-C TGA GAT GGA-3' | (SEQ ID NO:531) |
| 5'-TGA GAT GGA GGG CGG CAT GGC GGG CAC AGG CTG GGC-3' | (SEQ ID NO:532) |
| 5'-TGA GAT GGA GGG CGG CAT GGC GGG CAC AGG CTG GG-3' | (SEQ ID NO:533) |
| 5'-TGA GAT GGA GGG CGG CAT GGC GGG CAC AGG CTG G-3' | (SEQ ID NO:534) |
| 5'-TGA GAT GGA GGG CGG CAT GGC GGG CAC AGG CTG-3' | (SEQ ID NO:535) |
| 5'-TGA GAT GGA GGG CGG CAT GGC GGG CAC AGG CT-3' | (SEQ ID NO:536) |
| 5'-TGA GAT GGA GGG CGG CAT GGC GGG CAC AGG C-3' | (SEQ ID NO:537) |
| 5'-TGA GAT GGA GGG CGG CAT GGC GGG CAC AGG-3' | (SEQ ID NO:538) |
| 5'-TGA GAT GGA GGG CGG CAT GGC GGG CAC AG-3' | (SEQ ID NO:539) |
| 5'-TGA GAT GGA GGG CGG CAT GGC GGG CAC A-3' | (SEQ ID NO:540) |
| 5'-TGA GAT GGA GGG CGG CAT GGC GGG CAC-3' | (SEQ ID NO:541) |
| 5'-TGA GAT GGA GGG CGG CAT GGC GGG CA-3' | (SEQ ID NO:542) |
| 5'-TGA GAT GGA GGG CGG CAT GGC GGG C-3' | (SEQ ID NO:543) |
| 5'-TGA GAT GGA GGG CGG CAT GGC GGG-3' | (SEQ ID NO:544) |
| 5'-TGA GAT GGA GGG CGG CAT GGC GG-3' | (SEQ ID NO:545) |
| 5'-TGA GAT GGA GGG CGG CAT GGC G-3' | (SEQ ID NO:546) |
| 5'-TGA GAT GGA GGG CGG CAT GGC-3' | (SEQ ID NO:547) |

-continued

| | |
|---|---|
| 5'-TGA GAT GGA GGG CGG CAT GG-3' | (SEQ ID NO:548) |
| 5'-TGA GAT GGA GGG CGG CAT G-3' | (SEQ ID NO:549) |
| 5'-TGA GAT GGA GGG CGG CAT-3' | (SEQ ID NO:550) |
| 5'-TGA GAT GGA GGG CGG CA-3' | (SEQ ID NO:551) |
| 5'-TGA GAT GGA GGG CGG C-3' | (SEQ ID NO:552) |
| 5'-TGA GAT GGA GGG CGG-3' | (SEQ ID NO:553) |
| 5'-TGA GAT GGA GGG CG-3' | (SEQ ID NO:554) |
| 5'-TGA GAT GGA GGG C-3' | (SEQ ID NO:555) |
| 5'-TGA GAT GGA GGG-3' | (SEQ ID NO:556) |
| 5'-TGA GAT GGA GG-3' | (SEQ ID NO:557) |
| 5'-TGA GAT GGA G-3' | (SEQ ID NO:558) |
| 5'-GA GAT GGA GGG CGG CAT GGC GGG CAC AGG CTG GGC-3' | (SEQ ID NO:559) |
| 5'-GA GAT GGA GGG CGG CAT GGC GGG CAC AGG CTG GG-3' | (SEQ ID NO:560) |
| 5'-GA GAT GGA GGG CGG CAT GGC GGG CAC AGG CTG G-3' | (SEQ ID NO:561) |
| 5'-GA GAT GGA GGG CGG CAT GGC GGG CAC AGG CTG-3' | (SEQ ID NO:562) |
| 5'-GA GAT GGA GGG CGG CAT GGC GGG CAC AGG CT-3' | (SEQ ID NO:563) |
| 5'-GA GAT GGA GGG CGG CAT GGC GGG CAC AGG C-3' | (SEQ ID NO:564) |
| 5'-GA GAT GGA GGG CGG CAT GGC GGG CAC AGG-3' | (SEQ ID NO:565) |
| 5'-GA GAT GGA GGG CGG CAT GGC GGG CAC AG-3' | (SEQ ID NO:566) |
| 5'-GA GAT GGA GGG CGG CAT GGC GGG CAC A-3' | (SEQ ID NO:567) |
| 5'-GA GAT GGA GGG CGG CAT GGC GGG CAC-3' | (SEQ ID NO:568) |
| 5'-GA GAT GGA GGG CGG CAT GGC GGG CA-3' | (SEQ ID NO:569) |
| 5'-GA GAT GGA GGG CGG CAT GGC GGG C-3' | (SEQ ID NO:570) |
| 5'-GA GAT GGA GGG CGG CAT GGC GGG-3' | (SEQ ID NO:571) |
| 5'-GA GAT GGA GGG CGG CAT GGC GG-3' | (SEQ ID NO:572) |
| 5'-GA GAT GGA GGG CGG CAT GGC G-3' | (SEQ ID NO:573) |
| 5'-GA GAT GGA GGG CGG CAT GGC-3' | (SEQ ID NO:574) |
| 5'-GA GAT GGA GGG CGG CAT GG-3' | (SEQ ID NO:575) |

-continued

| | |
|---|---|
| 5'-GA GAT GGA GGG CGG CAT G-3' | (SEQ ID NO:576) |
| 5'-GA GAT GGA GGG CGG CAT-3' | (SEQ ID NO:577) |
| 5'-GA GAT GGA GGG CGG CA-3' | (SEQ ID NO:578) |
| 5'-GA GAT GGA GGG CGG C-3' | (SEQ ID NO:579) |
| 5'-GA GAT GGA GGG CGG-3' | (SEQ ID NO:580) |
| 5'-GA GAT GGA GGG CG-3' | (SEQ ID NO:581) |
| 5'-GA GAT GGA GGG C-3' | (SEQ ID NO:582) |
| 5'-GA GAT GGA GGG-3' | (SEQ ID NO:583) |
| 5'-GA GAT GGA GG-3' | (SEQ ID NO:584) |
| 5'-A GAT GGA GGG CGG CAT GGC GGG CAC AGG CTG GGC-3' | (SEQ ID NO:585) |
| 5'-A GAT GGA GGG CGG CAT GGC GGG CAC AGG CTG GG-3' | (SEQ ID NO:586) |
| 5'-A GAT GGA GGG CGG CAT GGC GGG CAC AGG CTG G-3' | (SEQ ID NO:587) |
| 5'-A GAT GGA GGG CGG CAT GGC GGG CAC AGG CTG-3' | (SEQ ID NO:588) |
| 5'-A GAT GGA GGG CGG CAT GGC GGG CAC AGG CT-3' | (SEQ ID NO:589) |
| 5'-A GAT GGA GGG CGG CAT GGC GGG CAC AGG C-3' | (SEQ ID NO:590) |
| 5'-A GAT GGA GGG CGG CAT GGC GGG CAC AGG-3' | (SEQ ID NO:591) |
| 5'-A GAT GGA GGG CGG CAT GGC GGG CAC AG-3' | (SEQ ID NO:592) |
| 5'-A GAT GGA GGG CGG CAT GGC GGG CAC A-3' | (SEQ ID NO:593) |
| 5'-A GAT GGA GGG CGG CAT GGC GGG CAC-3' | (SEQ ID NO:594) |
| 5'-A GAT GGA GGG CGG CAT GGC GGG CA-3' | (SEQ ID NO:595) |
| 5'-A GAT GGA GGG CGG CAT GGC GGG C-3' | (SEQ ID NO:596) |
| 5'-A GAT GGA GGG CGG CAT GGC GGG-3' | (SEQ ID NO:597) |
| 5'-A GAT GGA GGG CGG CAT GGC GG-3' | (SEQ ID NO:598) |
| 5'-A GAT GGA GGG CGG CAT GGC G-3' | (SEQ ID NO:599) |
| 5'-A GAT GGA GGG CGG CAT GGC-3' | (SEQ ID NO:600) |
| 5'-A GAT GGA GGG CGG CAT GG-3' | (SEQ ID NO:601) |
| 5'-A GAT GGA GGG CGG CAT G-3' | (SEQ ID NO:602) |
| 5'-A GAT GGA GGG CGG CAT-3' | (SEQ ID NO:603) |

-continued

| | |
|---|---|
| 5'-A GAT GGA GGG CGG CA-3' | (SEQ ID NO:604) |
| 5'-A GAT GGA GGG CGG C-3' | (SEQ ID NO:605) |
| 5'-A GAT GGA GGG CGG-3' | (SEQ ID NO:606) |
| 5'-A GAT GGA GGG CG-3' | (SEQ ID NO:607) |
| 5'-A GAT GGA GGG C-3' | (SEQ ID NO:608) |
| 5'-A GAT GGA GGG-3' | (SEQ ID NO:609) |
| 5'-GAT GGA GGG CGG CAT GGC GGG CAC AGG CTG GGC-3' | (SEQ ID NO:610) |
| 5'-GAT GGA GGG CGG CAT GGC GGG CAC AGG CTG GG-3' | (SEQ ID NO:611) |
| 5'-GAT GGA GGG CGG CAT GGC GGG CAC AGG CTG G-3' | (SEQ ID NO:612) |
| 5'-GAT GGA GGG CGG CAT GGC GGG CAC AGG CTG-3' | (SEQ ID NO:613) |
| 5'-GAT GGA GGG CGG CAT GGC GGG CAC AGG CT-3' | (SEQ ID NO:614) |
| 5'-GAT GGA GGG CGG CAT GGC GGG CAC AGG C-3' | (SEQ ID NO:615) |
| 5'-GAT GGA GGG CGG CAT GGC GGG CAC AGG-3' | (SEQ ID NO:616) |
| 5'-GAT GGA GGG CGG CAT GGC GGG CAC AG-3' | (SEQ ID NO:617) |
| 5'-GAT GGA GGG CGG CAT GGC GGG CAC A-3' | (SEQ ID NO:618) |
| 5'-GAT GGA GGG CGG CAT GGC GGG CAC-3' | (SEQ ID NO:619) |
| 5'-GAT GGA GGG CGG CAT GGC GGG CA-3' | (SEQ ID NO:620) |
| 5'-GAT GGA GGG CGG CAT GGC GGG C-3' | (SEQ ID NO:621) |
| 5'-GAT GGA GGG CGG CAT GGC GGG-3' | (SEQ ID NO:622) |
| 5'-GAT GGA GGG CGG CAT GGC GG-3' | (SEQ ID NO:623) |
| 5'-GAT GGA GGG CGG CAT GGC G-3' | (SEQ ID NO:624) |
| 5'-GAT GGA GGG CGG CAT GGC-3' | (SEQ ID NO:625) |
| 5'-GAT GGA GGG CGG CAT GG-3' | (SEQ ID NO:626) |
| 5'-GAT GGA GGG CGG CAT G-3' | (SEQ ID NO:627) |
| 5'-GAT GGA GGG CGG CAT-3' | (SEQ ID NO:628) |
| 5'-GAT GGA GGG CGG CA-3' | (SEQ ID NO:629) |
| 5'-GAT GGA GGG CGG C-3' | (SEQ ID NO:630) |
| 5'-GAT GGA GGG CGG-3' | (SEQ ID NO:631) |

-continued

| | |
|---|---|
| 5'-GAT GGA GGG CG-3' | (SEQ ID NO:632) |
| 5'-GAT GGA GGG C-3' | (SEQ ID NO:633) |
| 5'-AT GGA GGG CGG CAT GGC GGG CAC AGG CTG GGC-3' | (SEQ ID NO:634) |
| 5'-AT GGA GGG CGG CAT GGC GGG CAC AGG CTG GG-3' | (SEQ ID NO:635) |
| 5'-AT GGA GGG CGG CAT GGC GGG CAC AGG CTG G-3' | (SEQ ID NO:636) |
| 5'-AT GGA GGG CGG CAT GGC GGG CAC AGG CTG-3' | (SEQ ID NO:637) |
| 5'-AT GGA GGG CGG CAT GGC GGG CAC AGG CT-3' | (SEQ ID NO:638) |
| 5'-AT GGA GGG CGG CAT GGC GGG CAC AGG C-3' | (SEQ ID NO:639) |
| 5'-AT GGA GGG CGG CAT GGC GGG CAC AGG-3' | (SEQ ID NO:640) |
| 5'-AT GGA GGG CGG CAT GGC GGG CAC AG-3' | (SEQ ID NO:641) |
| 5'-AT GGA GGG CGG CAT GGC GGG CAC A-3' | (SEQ ID NO:642) |
| 5'-AT GGA GGG CGG CAT GGC GGG CAC-3' | (SEQ ID NO:643) |
| 5'-AT GGA GGG CGG CAT GGC GGG CA-3' | (SEQ ID NO:644) |
| 5'-AT GGA GGG CGG CAT GGC GGG C-3' | (SEQ ID NO:645) |
| 5'-AT GGA GGG CGG CAT GGC GGG-3' | (SEQ ID NO:646) |
| 5'-AT GGA GGG CGG CAT GGC GG-3' | (SEQ ID NO:647) |
| 5'-AT GGA GGG CGG CAT GGC G-3' | (SEQ ID NO:648) |
| 5'-AT GGA GGG CGG CAT GGC-3' | (SEQ ID NO:649) |
| 5'-AT GGA GGG CGG CAT GG-3' | (SEQ ID NO:650) |
| 5'-AT GGA GGG CGG CAT G-3' | (SEQ ID NO:651) |
| 5'-AT GGA GGG CGG CAT-3' | (SEQ ID NO:652) |
| 5'-AT GGA GGG CGG CA-3' | (SEQ ID NO:653) |
| 5'-AT GGA GGG CGG C-3' | (SEQ ID NO:654) |
| 5'-AT GGA GGG CGG-3' | (SEQ ID NO:655) |
| 5'-AT GGA GGG CG-3' | (SEQ ID NO:656) |
| 5'-T GGA GGG CGG CAT GGC GGG CAC AGG CTG GGC-3' | (SEQ ID NO:657) |
| 5'-T GGA GGG CGG CAT GGC GGG CAC AGG CTG GG-3' | (SEQ ID NO:658) |
| 5'-T GGA GGG CGG CAT GGC GGG CAC AGG CTG G-3' | (SEQ ID NO:659) |

-continued

| | |
|---|---|
| 5'-T GGA GGG CGG CAT GGC GGG CAC AGG CTG-3' | (SEQ ID NO:660) |
| 5'-T GGA GGG CGG CAT GGC GGG CAC AGG CT-3' | (SEQ ID NO:661) |
| 5'-T GGA GGG CGG CAT GGC GGG CAC AGG C-3' | (SEQ ID NO:662) |
| 5'-T GGA GGG CGG CAT GGC GGG CAC AGG-3' | (SEQ ID NO:663) |
| 5'-T GGA GGG CGG CAT GGC GGG CAC AG-3' | (SEQ ID NO:664) |
| 5'-T GGA GGG CGG CAT GGC GGG CAC A-3' | (SEQ ID NO:665) |
| 5'-T GGA GGG CGG CAT GGC GGG CAC-3' | (SEQ ID NO:666) |
| 5'-T GGA GGG CGG CAT GGC GGG CA-3' | (SEQ ID NO:667) |
| 5'-T GGA GGG CGG CAT GGC GGG C-3' | (SEQ ID NO:668) |
| 5'-T GGA GGG CGG CAT GGC GGG-3' | (SEQ ID NO:669) |
| 5'-T GGA GGG CGG CAT GGC GG-3' | (SEQ ID NO:670) |
| 5'-T GGA GGG CGG CAT GGC G-3' | (SEQ ID NO:671) |
| 5'-T GGA GGG CGG CAT GGC-3' | (SEQ ID NO:672) |
| 5'-T GGA GGG CGG CAT GG-3' | (SEQ ID NO:673) |
| 5'-T GGA GGG CGG CAT G-3' | (SEQ ID NO:674) |
| 5'-T GGA GGG CGG CAT-3' | (SEQ ID NO:675) |
| 5'-T GGA GGG CGG CA-3' | (SEQ ID NO:676) |
| 5'-T GGA GGG CGG C-3' | (SEQ ID NO:677) |
| 5'-T GGA GGG CGG-3' | (SEQ ID NO:678) |
| 5'-GGA GGG CGG CAT GGC GGG CAC AGG CTG GGC-3' | (SEQ ID NO:679) |
| 5'-GGA GGG CGG CAT GGC GGG CAC AGG CTG GG-3' | (SEQ ID NO:680) |
| 5'-GGA GGG CGG CAT GGC GGG CAC AGG CTG G-3' | (SEQ ID NO:681) |
| 5'-GGA GGG CGG CAT GGC GGG CAC AGG CTG-3' | (SEQ ID NO:682) |
| 5'-GGA GGG CGG CAT GGC GGG CAC AGG CT-3' | (SEQ ID NO:683) |
| 5'-GGA GGG CGG CAT GGC GGG CAC AGG C-3' | (SEQ ID NO:684) |
| 5'-GGA GGG CGG CAT GGC GGG CAC AGG-3' | (SEQ ID NO:685) |
| 5'-GGA GGG CGG CAT GGC GGG CAC AG-3' | (SEQ ID NO:686) |
| 5'-GGA GGG CGG CAT GGC GGG CAC A-3' | (SEQ ID NO:687) |

-continued

| | |
|---|---|
| 5'-GGA GGG CGG CAT GGC GGG CAC-3' | (SEQ ID NO:688) |
| 5'-GGA GGG CGG CAT GGC GGG CA-3' | (SEQ ID NO:689) |
| 5'-GGA GGG CGG CAT GGC GGG C-3' | (SEQ ID NO:690) |
| 5'-GGA GGG CGG CAT GGC GGG-3' | (SEQ ID NO:691) |
| 5'-GGA GGG CGG CAT GGC GG-3' | (SEQ ID NO:692) |
| 5'-GGA GGG CGG CAT GGC G-3' | (SEQ ID NO:693) |
| 5'-GGA GGG CGG CAT GGC-3' | (SEQ ID NO:694) |
| 5'-GGA GGG CGG CAT GG-3' | (SEQ ID NO:695) |
| 5'-GGA GGG CGG CAT G-3' | (SEQ ID NO:696) |
| 5'-GGA GGG CGG CAT-3' | (SEQ ID NO:697) |
| 5'-GGA GGG CGG CA-3' | (SEQ ID NO:698) |
| 5'-GGA GGG CGG C-3' | (SEQ ID NO:699) |
| 5'-GA GGG CGG CAT GGC GGG CAC AGG CTG GGC-3' | (SEQ ID NO:700) |
| 5'-GA GGG CGG CAT GGC GGG CAC AGG CTG GG-3' | (SEQ ID NO:701) |
| 5'-GA GGG CGG CAT GGC GGG CAC AGG CTG G-3' | (SEQ ID NO:702) |
| 5'-GA GGG CGG CAT GGC GGG CAC AGG CTG-3' | (SEQ ID NO:703) |
| 5'-GA GGG CGG CAT GGC GGG CAC AGG CT-3' | (SEQ ID NO:704) |
| 5'-GA GGG CGG CAT GGC GGG CAC AGG C-3' | (SEQ ID NO:705) |
| 5'-GA GGG CGG CAT GGC GGG CAC AGG-3' | (SEQ ID NO:706) |
| 5'-GA GGG CGG CAT GGC GGG CAC AG-3' | (SEQ ID NO:707) |
| 5'-GA GGG CGG CAT GGC GGG CAC A-3' | (SEQ ID NO:708) |
| 5'-GA GGG CGG CAT GGC GGG CAC-3' | (SEQ ID NO:709) |
| 5'-GA GGG CGG CAT GGC GGG CA-3' | (SEQ ID NO:710) |
| 5'-GA GGG CGG CAT GGC GGG C-3' | (SEQ ID NO:711) |
| 5'-GA GGG CGG CAT GGC GGG-3' | (SEQ ID NO:712) |
| 5'-GA GGG CGG CAT GGC GG-3' | (SEQ ID NO:713) |
| 5'-GA GGG CGG CAT GGC G-3' | (SEQ ID NO:714) |
| 5'-GA GGG CGG CAT GGC-3' | (SEQ ID NO:715) |

-continued

| | |
|---|---|
| 5'-GA GGG CGG CAT GG-3' | (SEQ ID NO:716) |
| 5'-GA GGG CGG CAT G-3' | (SEQ ID NO:717) |
| 5'-GA GGG CGG CAT-3' | (SEQ ID NO:718) |
| 5'-GA GGG CGG CA-3' | (SEQ ID NO:719) |
| 5'-A GGG CGG CAT GGC GGG CAC AGG CTG GGC-3' | (SEQ ID NO:720) |
| 5'-A GGG CGG CAT GGC GGG CAC AGG CTG GG-3' | (SEQ ID NO:721) |
| 5'-A GGG CGG CAT GGC GGG CAC AGG CTG G-3' | (SEQ ID NO:722) |
| 5'-A GGG CGG CAT GGC GGG CAC AGG CTG-3' | (SEQ ID NO:723) |
| 5'-A GGG CGG CAT GGC GGG CAC AGG CT-3' | (SEQ ID NO:724) |
| 5'-A GGG CGG CAT GGC GGG CAC AGG C-3' | (SEQ ID NO:725) |
| 5'-A GGG CGG CAT GGC GGG CAC AGG-3' | (SEQ ID NO:726) |
| 5'-A GGG CGG CAT GGC GGG CAC AG-3' | (SEQ ID NO:727) |
| 5'-A GGG CGG CAT GGC GGG CAC A-3' | (SEQ ID NO:728) |
| 5'-A GGG CGG CAT GGC GGG CAC-3' | (SEQ ID NO:729) |
| 5'-A GGG CGG CAT GGC GGG CA-3' | (SEQ ID NO:730) |
| 5'-A GGG CGG CAT GGC GGG C-3' | (SEQ ID NO:731) |
| 5'-A GGG CGG CAT GGC GGG-3' | (SEQ ID NO:732) |
| 5'-A GGG CGG CAT GGC GG-3' | (SEQ ID NO:733) |
| 5'-A GGG CGG CAT GGC G-3' | (SEQ ID NO:734) |
| 5'-A GGG CGG CAT GGC-3' | (SEQ ID NO:735) |
| 5'-A GGG CGG CAT GG-3' | (SEQ ID NO:736) |
| 5'-A GGG CGG CAT G-3' | (SEQ ID NO:737) |
| 5'-A GGG CGG CAT-3' | (SEQ ID NO:738) |
| 5'-GGG CGG CAT GGC GGG CAC AGG CTG GGC-3' | (SEQ ID NO:739) |
| 5'-GGG CGG CAT GGC GGG CAC AGG CTG GG-3' | (SEQ ID NO:740) |
| 5'-GGG CGG CAT GGC GGG CAC AGG CTG G-3' | (SEQ ID NO:741) |
| 5'-GGG CGG CAT GGC GGG CAC AGG CTG-3' | (SEQ ID NO:742) |
| 5'-GGG CGG CAT GGC GGG CAC AGG CT-3' | (SEQ ID NO:743) |

-continued

| | |
|---|---|
| 5'-GGG CGG CAT GGC GGG CAC AGG C-3' | (SEQ ID NO:744) |
| 5'-GGG CGG CAT GGC GGG CAC AGG-3' | (SEQ ID NO:745) |
| 5'-GGG CGG CAT GGC GGG CAC AG-3' | (SEQ ID NO:746) |
| 5'-GGG CGG CAT GGC GGG CAC A-3' | (SEQ ID NO:747) |
| 5'-GGG CGG CAT GGC GGG CAC-3' | (SEQ ID NO:748) |
| 5'-GGG CGG CAT GGC GGG CA-3' | (SEQ ID NO:749) |
| 5'-GGG CGG CAT GGC GGG C-3' | (SEQ ID NO:750) |
| 5'-GGG CGG CAT GGC GGG-3' | (SEQ ID NO:751) |
| 5'-GGG CGG CAT GGC GG-3' | (SEQ ID NO:752) |
| 5'-GGG CGG CAT GGC G-3' | (SEQ ID NO:753) |
| 5'-GGG CGG CAT GGC-3' | (SEQ ID NO:754) |
| 5'-GGG CGG CAT GG-3' | (SEQ ID NO:755) |
| 5'-GGG CGG CAT G-3' | (SEQ ID NO:756) |
| 5'-GG CGG CAT GGC GGG CAC AGG CTG GGC-3' | (SEQ ID NO:757) |
| 5'-GG CGG CAT GGC GGG CAC AGG CTG GG-3' | (SEQ ID NO:758) |
| 5'-GG CGG CAT GGC GGG CAC AGG CTG G-3' | (SEQ ID NO:759) |
| 5'-GG CGG CAT GGC GGG CAC AGG CTG-3' | (SEQ ID NO:760) |
| 5'-GG CGG CAT GGC GGG CAC AGG CT-3' | (SEQ ID NO:761) |
| 5'-GG CGG CAT GGC GGG CAC AGG C-3' | (SEQ ID NO:762) |
| 5'-GG CGG CAT GGC GGG CAC AGG-3' | (SEQ ID NO:763) |
| 5'-GG CGG CAT GGC GGG CAC AG-3' | (SEQ ID NO:764) |
| 5'-GG CGG CAT GGC GGG CAC A-3' | (SEQ ID NO:765) |
| 5'-GG CGG CAT GGC GGG CAC-3' | (SEQ ID NO:766) |
| 5'-GG CGG CAT GGC GGG CA-3' | (SEQ ID NO:767) |
| 5'-GG CGG CAT GGC GGG C-3' | (SEQ ID NO:768) |
| 5'-GG CGG CAT GGC GGG-3' | (SEQ ID NO:769) |
| 5'-GG CGG CAT GGC GG-3' | (SEQ ID NO:770) |
| 5'-GG CGG CAT GGC G-3' | (SEQ ID NO:771) |

-continued

| | |
|---|---|
| 5'-GG CGG CAT GGC-3' | (SEQ ID NO:772) |
| 5'-GG CGG CAT GG-3' | (SEQ ID NO:773) |
| 5'-G CGG CAT GGC GGG CAC AGG CTG GGC-3' | (SEQ ID NO:774) |
| 5'-G CGG CAT GGC GGG CAC AGG CTG GG-3' | (SEQ ID NO:775) |
| 5'-G CGG CAT GGC GGG CAC AGG CTG G-3' | (SEQ ID NO:776) |
| 5'-G CGG CAT GGC GGG CAC AGG CTG-3' | (SEQ ID NO:777) |
| 5'-G CGG CAT GGC GGG CAC AGG CT-3' | (SEQ ID NO:778) |
| 5'-G CGG CAT GGC GGG CAC AGG C-3' | (SEQ ID NO:779) |
| 5'-G CGG CAT GGC GGG CAC AGG-3' | (SEQ ID NO:780) |
| 5'-G CGG CAT GGC GGG CAC AG-3' | (SEQ ID NO:781) |
| 5'-G CGG CAT GGC GGG CAC A-3' | (SEQ ID NO:782) |
| 5'-G CGG CAT GGC GGG CAC-3' | (SEQ ID NO:783) |
| 5'-G CGG CAT GGC GGG CA-3' | (SEQ ID NO:784) |
| 5'-G CGG CAT GGC GGG C-3' | (SEQ ID NO:785) |
| 5'-G CGG CAT GGC GGG-3' | (SEQ ID NO:786) |
| 5'-G CGG CAT GGC GG-3' | (SEQ ID NO:787) |
| 5'-G CGG CAT GGC G-3' | (SEQ ID NO:788) |
| 5'-G CGG CAT GGC-3' | (SEQ ID NO:789) |
| 5'-CGG CAT GGC GGG CAC AGG CTG GGC-3' | (SEQ ID NO:790) |
| 5'-CGG CAT GGC GGG CAC AGG CTG GG-3' | (SEQ ID NO:791) |
| 5'-CGG CAT GGC GGG CAC AGG CTG G-3' | (SEQ ID NO:792) |
| 5'-CGG CAT GGC GGG CAC AGG CTG-3' | (SEQ ID NO:793) |
| 5'-CGG CAT GGC GGG CAC AGG CT-3' | (SEQ ID NO:794) |
| 5'-CGG CAT GGC GGG CAC AGG C-3' | (SEQ ID NO:795) |
| 5'-CGG CAT GGC GGG CAC AGG-3' | (SEQ ID NO:796) |
| 5'-CGG CAT GGC GGG CAC AG-3' | (SEQ ID NO:797) |
| 5'-CGG CAT GGC GGG CAC A-3' | (SEQ ID NO:798) |
| 5'-CGG CAT GGC GGG CAC-3' | (SEQ ID NO:799) |

-continued

5'-CGG CAT GGC GGG CA-3' (SEQ ID NO:800)

5'-CGG CAT GGC GGG C-3' (SEQ ID NO:801)

5'-CGG CAT GGC GGG-3' (SEQ ID NO:802)

5'-CGG CAT GGC GG-3' (SEQ ID NO:803)

5'-CGG CAT GGC G-3' (SEQ ID NO:804)

5'-GG CAT GGC GGG CAC AGG CTG GGC-3' (SEQ ID NO:805)

5'-GG CAT GGC GGG CAC AGG CTG GG-3' (SEQ ID NO:806)

5'-GG CAT GGC GGG CAC AGG CTG G-3' (SEQ ID NO:807)

5'-GG CAT GGC GGG CAC AGG CTG-3' (SEQ ID NO:808)

5'-GG CAT GGC GGG CAC AGG CT-3' (SEQ ID NO:809)

5'-GG CAT GGC GGG CAC AGG C-3' (SEQ ID NO:810)

5'-GG CAT GGC GGG CAC AGG-3' (SEQ ID NO:811)

5'-GG CAT GGC GGG CAC AG-3' (SEQ ID NO:812)

5'-GG CAT GGC GGG CAC A-3' (SEQ ID NO:813)

5'-GG CAT GGC GGG CAC-3' (SEQ ID NO:814)

5'-GG CAT GGC GGG CA-3' (SEQ ID NO:815)

5'-GG CAT GGC GGG C-3' (SEQ ID NO:816)

5'-GG CAT GGC GGG-3' (SEQ ID NO:817)

5'-GG CAT GGC GG-3' (SEQ ID NO:818)

5'-G CAT GGC GGG CAC AGG CTG GGC-3' (SEQ ID NO:819)

5'-G CAT GGC GGG CAC AGG CTG GG-3' (SEQ ID NO:820)

5'-G CAT GGC GGG CAC AGG CTG G-3' (SEQ ID NO:821)

5'-G CAT GGC GGG CAC AGG CTG-3' (SEQ ID NO:822)

5'-G CAT GGC GGG CAC AGG CT-3' (SEQ ID NO:823)

5'-G CAT GGC GGG CAC AGG C-3' (SEQ ID NO:824)

5'-G CAT GGC GGG CAC AGG-3' (SEQ ID NO:825)

5'-G CAT GGC GGG CAC AG-3' (SEQ ID NO:826)

5'-G CAT GGC GGG CAC A-3' (SEQ ID NO:827)

-continued

| | |
|---|---|
| 5'-G CAT GGC GGG CAC-3' | (SEQ ID NO:828) |
| 5'-G CAT GGC GGG CA-3' | (SEQ ID NO:829) |
| 5'-G CAT GGC GGG C-3' | (SEQ ID NO:830) |
| 5'-G CAT GGC GGG-3' | (SEQ ID NO:831) |
| 5'-CAT GGC GGG CAC AGG CTG GGC-3' | (SEQ ID NO:832) |
| 5'-CAT GGC GGG CAC AGG CTG GG-3' | (SEQ ID NO:833) |
| 5'-CAT GGC GGG CAC AGG CTG G-3' | (SEQ ID NO:834) |
| 5'-CAT GGC GGG CAC AGG CTG-3' | (SEQ ID NO:835) |
| 5'-CAT GGC GGG CAC AGG CT-3' | (SEQ ID NO:836) |
| 5'-CAT GGC GGG CAC AGG C-3' | (SEQ ID NO:837) |
| 5'-CAT GGC GGG CAC AGG-3' | (SEQ ID NO:838) |
| 5'-CAT GGC GGG CAC AG-3' | (SEQ ID NO:839) |
| 5'-CAT GGC GGG CAC A-3' | (SEQ ID NO:840) |
| 5'-CAT GGC GGG CAC-3' | (SEQ ID NO:841) |
| 5'-CAT GGC GGG CA-3' | (SEQ ID NO:842) |
| 5'-CAT GGC GGG C-3' | (SEQ ID NO:843) |
| 5'-AT GGC GGG CAC AGG CTG GGC-3' | (SEQ ID NO:844) |
| 5'-AT GGC GGG CAC AGG CTG GG-3' | (SEQ ID NO:845) |
| 5'-AT GGC GGG CAC AGG CTG G-3' | (SEQ ID NO:846) |
| 5'-AT GGC GGG CAC AGG CTG-3' | (SEQ ID NO:847) |
| 5'-AT GGC GGG CAC AGG CT-3' | (SEQ ID NO:848) |
| 5'-AT GGC GGG CAC AGG C-3' | (SEQ ID NO:849) |
| 5'-AT GGC GGG CAC AGG-3' | (SEQ ID NO:850) |
| 5'-AT GGC GGG CAC AG-3' | (SEQ ID NO:851) |
| 5'-AT GGC GGG CAC A-3' | (SEQ ID NO:852) |
| 5'-AT GGC GGG CAC-3' | (SEQ ID NO:853) |
| 5'-AT GGC GGG CA-3' | (SEQ ID NO:854) |
| 5'-T GGC GGG CAC AGG CTG GGC-3' | (SEQ ID NO:855) |

-continued

| | |
|---|---|
| 5'-T GGC GGG CAC AGG CTG GG-3' | (SEQ ID NO:856) |
| 5'-T GGC GGG CAC AGG CTG G-3' | (SEQ ID NO:857) |
| 5'-T GGC GGG CAC AGG CTG-3' | (SEQ ID NO:858) |
| 5'-T GGC GGG CAC AGG CT-3' | (SEQ ID NO:859) |
| 5'-T GGC GGG CAC AGG C-3' | (SEQ ID NO:860) |
| 5'-T GGC GGG CAC AGG-3' | (SEQ ID NO:861) |
| 5'-T GGC GGG CAC AG-3' | (SEQ ID NO:862) |
| 5'-T GGC GGG CAC A-3' | (SEQ ID NO:863) |
| 5'-T GGC GGG CAC-3' | (SEQ ID NO:864) |
| 5'-GGC GGG CAC AGG CTG GGC-3' | (SEQ ID NO:865) |
| 5'-GGC GGG CAC AGG CTG GG-3' | (SEQ ID NO:866) |
| 5'-GGC GGG CAC AGG CTG G-3' | (SEQ ID NO:867) |
| 5'-GGC GGG CAC AGG CTG-3' | (SEQ ID NO:868) |
| 5'-GGC GGG CAC AGG CT-3' | (SEQ ID NO:869) |
| 5'-GGC GGG CAC AGG C-3' | (SEQ ID NO:870) |
| 5'-GGC GGG CAC AGG-3' | (SEQ ID NO:871) |
| 5'-GGC GGG CAC AG-3' | (SEQ ID NO:872) |
| 5'-GGC GGG CAC A-3' | (SEQ ID NO:873) |
| 5'-GC GGG CAC AGG CTG GGC-3' | (SEQ ID NO:874) |
| 5'-GC GGG CAC AGG CTG GG-3' | (SEQ ID NO:875) |
| 5'-GC GGG CAC AGG CTG G-3' | (SEQ ID NO:876) |
| 5'-GC GGG CAC AGG CTG-3' | (SEQ ID NO:877) |
| 5'-GC GGG CAC AGG CT-3' | (SEQ ID NO:878) |
| 5'-GC GGG CAC AGG C-3' | (SEQ ID NO:879) |
| 5'-GC GGG CAC AGG-3' | (SEQ ID NO:880) |
| 5'-GC GGG CAC AG-3' | (SEQ ID NO:881) |
| 5'-C GGG CAC AGG CTG GGC-3' | (SEQ ID NO:882) |
| 5'-C GGG CAC AGG CTG GG-3' | (SEQ ID NO:883) |

-continued

| | |
|---|---|
| 5'-C GGG CAC AGG CTG G-3' | (SEQ ID NO:884) |
| 5'-C GGG CAC AGG CTG-3' | (SEQ ID NO:885) |
| 5'-C GGG CAC AGG CT-3' | (SEQ ID NO:886) |
| 5'-C GGG CAC AGG C-3' | (SEQ ID NO:887) |
| 5'-C GGG CAC AGG-3' | (SEQ ID NO:888) |
| 5'-GGG CAC AGG CTG GGC-3' | (SEQ ID NO:889) |
| 5'-GGG CAC AGG CTG GG-3' | (SEQ ID NO:890) |
| 5'-GGG CAC AGG CTG G-3' | (SEQ ID NO:891) |
| 5'-GGG CAC AGG CTG-3' | (SEQ ID NO:892) |
| 5'-GGG CAC AGG CT-3' | (SEQ ID NO:893) |
| 5'-GGG CAC AGG C-3' | (SEQ ID NO:894) |
| 5'-GG CAC AGG CTG GGC-3' | (SEQ ID NO:895) |
| 5'-GG CAC AGG CTG GG-3' | (SEQ ID NO:896) |
| 5'-GG CAC AGG CTG G-3' | (SEQ ID NO:897) |
| 5'-GG CAC AGG CTG-3' | (SEQ ID NO:898) |
| 5'-GG CAC AGG CT-3' | (SEQ ID NO:899) |
| 5'-G CAC AGG CTG GGC-3' | (SEQ ID NO:900) |
| 5'-G CAC AGG CTG GG-3' | (SEQ ID NO:901) |
| 5'-G CAC AGG CTG G-3' | (SEQ ID NO:902) |
| 5'-G CAC AGG CTG-3' | (SEQ ID NO:903) |
| 5'-CAC AGG CTG GGC-3' | (SEQ ID NO:904) |
| 5'-CAC AGG CTG GG-3' | (SEQ ID NO:905) |
| 5'-CAC AGG CTG G-3' | (SEQ ID NO:906) |
| 5'-AC AGG CTG GGC-3' | (SEQ ID NO:907) |
| 5'-AC AGG CTG GG-3' | (SEQ ID NO:908) |
| 5'-C AGG CTG GGC-3' | (SEQ ID NO:909) |
| 5'-GGC GGC CTG GAA AGC TGA GAT GGA GGG CGG CAT GGC GGG CAC AGG CTG GGC-3' | (SEQ ID NO:910) |
| 5'-GC GGC CTG GAA AGC TGA GAT GGA GGG CGG CAT GGC GGG CAC AGG CTG GGC-3' | (SEQ ID NO:911) |

-continued

5'-C GGC CTG GAA AGC TGA GAT GGA GGG CGG CAT GGC GGG CAC AGG CTG GGC-3'  (SEQ ID NO:912)

5'-GGC CTG GAA AGC TGA GAT GGA GGG CGG CAT GGC GGG CAC AGG CTG GGC-3'  (SEQ ID NO:913)

5'-GC CTG GAA AGC TGA GAT GGA GGG CGG CAT GGC GGG CAC AGG CTG GGC-3'  (SEQ ID NO:914)

5'-C CTG GAA AGC TGA GAT GGA GGG CGG CAT GGC GGG CAC AGG CTG GGC-3'  (SEQ ID NO:915)

5'-CTG GAA AGC TGA GAT GGA GGG CGG CAT GGC GGG CAC AGG CTG GGC-3'  (SEQ ID NO:916)

5'-TG GAA AGC TGA GAT GGA GGG CGG CAT GGC GGG CAC AGG CTG GGC-3'  (SEQ ID NO:917)

5'-G GAA AGC TGA GAT GGA GGG CGG CAT GGC GGG CAC AGG CTG GGC-3'  (SEQ ID NO:918)

5'-GAA AGC TGA GAT GGA GGG CGG CAT GGC GGG CAC AGG CTG GGC-3'  (SEQ ID NO:919)

5'-AA AGC TGA GAT GGA GGG CGG CAT GGC GGG CAC AGG CTG GGC-3'  (SEQ ID NO:920)

5'-A AGC TGA GAT GGA GGG CGG CAT GGC GGG CAC AGG CTG GGC-3'  (SEQ ID NO:921)

5'-AGC TGA GAT GGA GGG CGG CAT GGC GGG CAC AGG CTG GGC-3'  (SEQ ID NO:922)

5'-GC TGA GAT GGA GGG CGG CAT GGC GGG CAC AGG CTG GGC-3'  (SEQ ID NO:923)

5'-C TGA GAT GGA GGG CGG CAT GGC GGG CAC AGG CTG GGC-3'  (SEQ ID NO:924)

5'-TGA GAT GGA GGG CGG CAT GGC GGG CAC AGG CTG GGC-3'  (SEQ ID NO:925)

5'-GA GAT GGA GGG CGG CAT GGC GGG CAC AGG CTG GGC-3'  (SEQ ID NO:926)

5'-A GAT GGA GGG CGG CAT GGC GGG CAC AGG CTG GGC-3'  (SEQ ID NO:927)

5'-GAT GGA GGG CGG CAT GGC GGG CAC AGG CTG GGC-3'  (SEQ ID NO:928)

5'-AT GGA GGG CGG CAT GGC GGG CAC AGG CTG GGC-3'  (SEQ ID NO:929)

5'-T GGA GGG CGG CAT GGC GGG CAC AGG CTG GGC-3'  (SEQ ID NO:930)

5'-GGA GGG CGG CAT GGC GGG CAC AGG CTG GGC-3'  (SEQ ID NO:931)

5'-GA GGG CGG CAT GGC GGG CAC AGG CTG GGC-3'  (SEQ ID NO:932)

5'-A GGG CGG CAT GGC GGG CAC AGG CTG GGC-3'  (SEQ ID NO:933)

5'-GGG CGG CAT GGC GGG CAC AGG CTG GGC-3'  (SEQ ID NO:934)

5'-GG CGG CAT GGC GGG CAC AGG CTG GGC-3'  (SEQ ID NO:935)

5'-G CGG CAT GGC GGG CAC AGG CTG GGC-3'  (SEQ ID NO:936)

5'-CGG CAT GGC GGG CAC AGG CTG GGC-3'  (SEQ ID NO:937)

5'-GG CAT GGC GGG CAC AGG CTG GGC-3'  (SEQ ID NO:938)

5'-G CAT GGC GGG CAC AGG CTG GGC-3'  (SEQ ID NO:939)

-continued

```
5'-CAT GGC GGG CAC AGG CTG GGC-3'                          (SEQ ID
                                                           NO:940)

5'-AT GGC GGG CAC AGG CTG GGC-3'                           (SEQ ID
                                                           NO:941)

5'-T GGC GGG CAC AGG CTG GGC-3'                            (SEQ ID
                                                           NO:942)

5'-GGC GGG CAC AGG CTG GGC-3'                              (SEQ ID
                                                           NO:943)

5'-GC GGG CAC AGG CTG GGC-3'                               (SEQ ID
                                                           NO:944)

5'-C GGG CAC AGG CTG GGC-3'                                (SEQ ID
                                                           NO:945)

5'-GGG CAC AGG CTG GGC-3'                                  (SEQ ID
                                                           NO:946)

5'-GG CAC AGG CTG GGC-3'                                   (SEQ ID
                                                           NO:947)

5'-G CAC AGG CTG GGC-3'                                    (SEQ ID
                                                           NO:948)

5'-CAC AGG CTG GGC-3'                                      (SEQ ID
                                                           NO:949)

5'-AC AGG CTG GGC-3'                                       (SEQ ID
                                                           NO:950)

5'-C AGG CTG GGC-3'                                        (SEQ ID
                                                           NO:951)

5'-AGG CTG GGC-3'                                          (SEQ ID
                                                           NO:952)
```

0

In the antisense oligonucleotides of the present invention, exemplified by the preceding sequences, adenosine bases may be replaced with an appropriate "spacer" or universal base (e.g., 1-[β-D-2'-deoxyribofuranosyl]-5-nitroindole], or with an adenosine agonist or antagonist that does not stimulate adenosine $A_1$ or $A_3$ receptors. Also parts of this invention are analogs of oligonucleotides in which, for example, the phosphodiester bonds have been modified, e.g., to a methylphosphonate, a phosphotriester, a phosphorothioate, a phosphorodithioate, or the phosphoramidate, so as to render the oligonucleotide more stable in vivo. The naturally occurring phosphodiester linkages in oligonucleotides are susceptible to degradation by endogenously occurring cellular nucleases, while many analogous linkages are highly resistant to nuclease degradation. See Milligan et al., and Cohen, J.S., supra. The use of a "3'-end cap" strategy by which nuclease-resistant linkages are substituted for phosphodiester linkages at the 3' end of the oligonucleotide protects oligonucleotides from degredation See Tidd, D. M. and Warenius, H. M., Br. J. Cancer 60, 343–350 (1989); Shaw, J. P. et al., Nucleic Acids Res. 19, 747–750 (1991). Phosphoramidate, phosphorothioate, and methylphosphonate linkages are suitable for use in this invention. In addition extensive modification of the phosphodiester backbone has been shown to impart stability and may allow for enhanced affinity and increased cellular permeation of oligonucleotides. See Milligan, et al., supra. Many different chemical strategies have been employed to replace the entire phosphodiester backbone with novel linkages. Id. The analogs of the oligonucleotides of the invention include phosphorothioate, phosphorodithioate, methylphosphonate, phosphoramidate, boranophosphate, phosphotriester, formacetal, 3'-thioformacetal, 5'-thioformacetal, 5'-thioether, carbonate, 5'-N-carbamate, sulfate, sulfonate, sulfamate, sulfonamide, sulfone, sulfite, sulfoxide, sulfide, hydroxylamine, methylene(methylimino) (MMI) or methyleneoxy(methylimino) (MOMI) linkages. Phosphorothioate and methylphosphonate-modified oligonucleotides are particularly preferred because of their availability through automated oligonucleotide synthesis. Id. Antisense oligonucleotides containing modifications to the nucleotide base itself (e.g., a C-5 propyne) or to the sugar (e.g., a carbohydrate modification), are also aspects of the present invention.

Where appropriate, the antisense oligonucleotides may be administered in the form of pharmaceutically acceptable salts.

Antisense oligonucleotides may be of any suitable length, e.g., from about 10 to 60 nucleotides in length, depending on the particular target being bound and their mode of delivery. Preferably the antisense oligonucleotide is directed to an mRNA region containing a junction between intron and exon. Where the antisense oligonucleotide is directed to an intron/exon junction, it may either entirely overlie the junction or may be sufficiently close to the junction to inhibit the splicing out of the intervening exon during processing of precursor mRNA to mature mRNA, e.g., with the 3' or 5' terminus of the antisense oligonucleotide being positioned within about, for example, 10, 5, 3, or 2 nucleotides of the intron/exon junction. Also preferred are antisense oligonucleotides which overlap the initiation codon.

When practicing the present invention, the antisense oligonucleotides administered may be related in origin to the species to which it is administered. When treating humans, the antisense may be derived from human sequences if desired.

Pharmaceutical compositions provided herein comprise an antisense oligonucleotide as given above. These compositions are administered in amounts effective to reduce expression of an $A_1$ or $A_3$ adenosine receptor by passing through a cell membrane and binding specifically with mRNA encoding an $A_1$ or $A_3$ adenosine receptor in the cell so as to prevent its translation. Such compositions are provided in a suitable pharmaceutically acceptable carrier, e.g., sterile pyrogen-free saline solution. The antisense oligonucleotides may additionally be formulated with a hydrophobic carrier capable of passing through a cell membrane, e.g., in a liposome, with the liposomes carried in a pharmaceutically acceptable aqueous carrier. The oligonucleotides may also be coupled to a substance which inactivates mRNA, such as a ribozyme. The present oligonucleotides may be administered to a subject in need of such treatment to inhibit the activation of $A_1$ or $A_3$ adenosine receptors, The pharmaceutical formulation may also contain chimeric molecules comprising antisense oligonucleotides attached to molecules which are known to be internalized by cells. These oligonucleotide conjugates utilize cellular uptake pathways to increase the cellular concentrations of oligonucleotides. Examples of macromolecules used in this manner include transferrin, asialoglycoprotein (bound to oligonucleotides via polylysine) and streptavidin.

In the pharmaceutical formulation the antisense compound may be contained within a lipid particle or vesicle, such as a liposome or microcrystal. The lipid particles may be of any suitable structure, such as unilamellar or plurilamellar, so long as the antisense oligonucleotide is contained therein. Positively charged lipids such as N-[1-(2,3-dioleoyloxi)propyl]-N,N,N-trimethyl-ammoniumethylsulfate, or "DOTAP," are particularly preferred for such particles and vesicles. The preparation of such lipid particles is well known. See, e.g., U.S. Pat. Nos. 4,880,635 to Janoff et al.; 4,906,477 to Kurono et al.; 4,911,928 to Wallach; 4,917,951 to Wallach; 4,920,016 to Allen et al.;4,921,757 to Wheatley et al.; etc.

The composition of the invention may be administered by any means which transports the antisense nucleotide composition to the lung. The antisense compounds disclosed herein may be administered to the lungs of a patient by any suitable means, but are preferably administered by inhalation of an aerosol comprised of respirable particles, which comprise the antisense compound. The respirable particles may be liquid or solid and they may optionally contain other therapeutic ingredients.

The antisense compound of the present invention should be administered as a formulation including particles of respirable size: that is, particles of a size sufficiently small to pass through the nose, mouth and larynx upon inhalation and through the bronchi and alveoli of the lungs. In general, respirable particles range from about 0.5 to 10 microns in size. Particles of non-respirable size which are included in the aerosol tend to deposit in the throat and be swallowed, and the quantity of of non-respirable particles in the aerosol is thus minimized. For nasal administration, a particle size in the range of 10–500 $\mu$m is preferred to ensure retention in the nasal cavity.

Liquid pharmaceutical compositions of active compound for producing an aerosol may be prepared by combining the antisense compound with a suitable vehicle, such as sterile pyrogen free water. Other therapeutic compounds may optionally be included.

Solid particulate compositions containing respirable dry particles of micronized antisense compound may be prepared by grinding dry antisense compound with a mortar and pestle, and then passing the micronized composition through a 400 mesh screen to break up or separate out large agglomerates. A solid particulate composition comprising the antisense compound may optionally contain a dispersant which serves to facilitate the formation of an aerosol as well as other therapeutic compounds. A suitable dispersant is lactose, which may be blended with the antisense compound in any suitable ratio, e.g., a 1 to 1 ratio by weight.

The dosage of the antisense compound administered will depend upon the disease being treated, the condition of the subject, the particular formulation, the route of administration, the timing of administration to a subject, etc. In general, intracellular concentrations of the oligonucleotide of from 0.05 to 50 $\mu$M, or more particularly 0.2 to 5 $\mu$M, are desired. For administration to a subject such as a human, a dosage of about 0.01, 0.1, or 1 mg/Kg up to 50, 100, or 150 mg/Kg or more is typically employed. Depending on the solubility of the particular formulation of active compound administered, the daily dose may be divided among one or several unit dose administrations. The administration of the antisense compounds may be carried out therapeutically, i.e., as a rescue treatment, or prophylactically.

The aerosols of liquid particles comprising the antisense compound may be produced by any suitable means, such as with a nebulizer. See, e.g., U.S. Pat. No. 4,501,729. Nebulizers are commercially available devices which transform solutions or suspensions of the active ingredient into a therapeutic aerosol mist either by means of acceleration of a compressed gas, typically air or oxygen, through a narrow venturi orifice or by means of ultrasonic agitation. Suitable formulations for use in nebulizers comprise the active ingredient in a liquid carrier in an amount up to 40% w/w preferably less than 20% w/w. the carrier is typically water or a dilute aqueous alcoholic solution, preferably made isotonic with body fluids by the addition of, for example, sodium chloride. Optional additives include preservatives if the formulation is not prepared sterile, for example, methyl hydroxybenzoate, antioxidants, flavoring agents, volatile oils, buffering agents and surfactants.

The aerosols of solid particles comprising the active compound may likewise be produced with any solid particulate medicament aerosol generator. Aerosol generators for administering solid particulate medicaments to a subject produce particles which are respirable, as explained above, and generate a volume of aerosol containing a predetermined metered dose of a medicament at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder, e.g., a metered dose thereof effective to carry out the treatments described herein is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation. A second type of illustrative aerosol generator comprises a metered dose inhaler. Metered dose inhalers are pressurized aerosol dispensers, typically containing a suspension or solution formulation of the active ingredient in a liquified propellant. During use these devices discharge the formulation through a valve adapted to deliver a metered volume, typically from 10 to 150 $\mu$l, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants, such as oleic acid or sorbitan trioleate, antioxidants and suitable flavoring agents.

The aerosol, whether formed from solid or liquid particles, may be produced by the aerosol generator at a rate of from about 10 to 150 liters per minute, more preferably from about 30 to 150 liters per minute, and most preferably about 60 liters per minute. Aerosols containing greater amounts of medicament may be administered more rapidly.

The following examples are provided to illustrate the present invention, and should not be construed as limiting thereon. In these examples, $\mu M$ means micromolar, mL means milliliters, $\mu m$ means micrometers, mm means millimeters, cm means centimeters, ° C. means degrees Celsius, $\mu g$ means micrograms, mg means milligrams, g means grams, kg means kilograms, M means molar, and h means hours.

EXAMPLES

Example 1
Design and Synthesis of Antisense Oligonucleotides

The design of antisense oligonucleotides against the $A_1$ and $A_1$ adenosine receptors may require the solution of the complex secondary structure of the target $A_1$ receptor mRNA and the target $A_3$ receptor mRNA. After generating this structure, antisense nucleotides are designed which target regions of mRNA which might be construed to confer functional activity or stability to the mRNA and which optimally may overlap the initiation codon. Other target sites are readily usable. As a demonstration of specificity of the antisense effect, other oligonucleotides not totally complementary to the target mRNA, but containing identical nucleotide compositions on a w/w basis, are included as controls in antisense experiments.

Adenosine $A_1$ receptor mRNA secondary structure was analyzed and used as described above to design a phosphorothioate antisense oligonucleotide. The antisense oligonucleotide which was synthesized was designated HAdA1AS and had the following sequence:

5'-GAT GGA GGG CGG CAT GGC GGG-3' (SEQ ID NO:1)

As a control, a mismatched phosphorothioate antisense nucleotide designated HAdA1MM was synthesized with the following sequence:

5'-GTA GCA GGC GGG GAT GGG GGC-3' (SEQ ID NO:2)

Each oligonucleotide had identical base content and general sequence structure. Homology searches in GENBANK (release 85.0) and EMBL (release 40.0) indicated that the antisense oligonucleotide was specific for the human and rabbit adenosine $A_1$ receptor genes, and that the mismatched control was not a candidate for hybridization with any known gene sequence.

Adenosine $A_3$ receptor mRNA secondary structure was similarly analyzed and used as described above to design two phosphorothioate antisense oligonucleotides. The first antisense oligonucleotide (HAdA3AS1) synthesized had the following sequence:

5'-GTT GTT GGG CAT CTT GCC-3' (SEQ ID NO:3)
As a control, a mismatched phosphorothioate antisense oligonucleotide (HAdA3MM1) was synthesized, having the following sequence:

5'-GTA CTT GCG GAT CTA GGC-3' (SEQ ID NO:4)

A second phosphorothioate antisense oligonucleotide (HAdA3AS2) was also designed and synthesized, having the following sequence:

5'-GTG GGC CTA GCT CTC GCC-3' (SEQ ID NO:5)
Its control oligonucleotide (HAdA3MM2) had the sequence:

5'-GTC GGG GTA CCT GTC GGC-3' (SEQ ID NO:6)

Phosphorothioate oligonucleotides were synthesized on an Applied Biosystems Model 396 Oligonucleotide Synthesizer, and purified using NENSORB chromatography (DuPont, Md.).

Example 2
Testing of $A_1$-Adenosine Receptor Antisense Oligonucleotides in Vitro The antisense oligonucleotide against the human $A_1$ receptor (SEQ ID NO:1) described above was tested for efficacy in an in vitro model utilizing lung adenocarcinoma cells HTB-54. HTB-54 lung adenocarcinoma cells were demonstrated to express the $A_1$ adenosine receptor using standard northern blotting procedures and receptor probes designed and synthesized in the laboratory.

HTB-54 human lung adenocarcinoma cells (106/100 mm tissue culture dish) were exposed to 5.0 $\mu M$ HAdA1AS or HAdA1MM for 24 hours, with a fresh change of media and oligonucleotides after 12 hours of incubation. Following 24 hour exposure to the oligonucleotides, cells were harvested and their RNA extracted by standard procedures. A 21-mer probe corresponding to the region of mRNA targeted by the antisense (and therefore having the same sequence as the antisense, but not phosphorothioated) was synthesized and used to probe northern blots of RNA prepared from HAdA1AS-treated, HAdA1MM-treated and non-treated HTB-54 cells. These blots showed clearly that HAdA1AS but not HAdA1MM effectively reduced human adenosine receptor mRNA by >50%. This result showed that HAdA1AS is a good candidate for an anti-asthma drug since it depletes intracellular mRNA for the adenosine $A_1$ receptor, which is involved in asthma.

Example 3
Efficacy of $A_1$-Adenosine Receptor Antisense Oligonucleotides in Vivo A fortuitous homology between the rabbit and human DNA sequences within the adenosine $A_1$ gene overlapping the initiation codon permitted the use of the phosphorothioate antisense oligonucleotides initially designed for use against the human adenosine $A_1$ receptor in a rabbit model.

Neonatal New Zealand white Pasteurella-free rabbits were immunized intraperitoneally within 24 hours of birth with 312 antigen units/mL house dustmite (*D. farinae*) extract (Berkeley Biologicals, Berkeley, Calif.), mixed with 10% kaolin. Immunizations were repeated weekly for the first month and then biweekly for the next 2 months. At 3–4 months of age, eight sensitized rabbits were anesthetized and relaxed with a mixture of ketamine hydrochloride (44 mg/kg) and acepromazine maleate (0.4 mg/kg) administered intramuscularly.

The rabbits were then laid supine in a comfortable position on a small molded, padded animal board and intubated with a 4.0-mm intratracheal tube (Mallinkrodt, Inc., Glens Falls, N.Y.). A polyethylene catheter of external diameter 2.4 mm with an attached latex balloon was passed into the esophagus and maintained at the same distance (approximately 16 cm) from the mouth throughout the experiments. The intratracheal tube was attached to a heated Fleisch pneumotachograph (size 00; DOM Medical, Richmond, Va.), and flow was measured using a Validyne differential pressure transducer (Model DP-45161927; Validyne Engineering Corp., Northridge, Calif.) driven by a Gould carrier amplifier (Model 11-4113; Gould Electronic, Cleveland, Ohio). The esophageal balloon was attached to one side of the differential pressure transducer, and the outflow of the intratracheal tube was connected to the opposite side of the pressure transducer to allow recording of transpulmonary pressure. Flow was integrated to give a continuous tidal volume, and measurements of total lung resistance (RL) and dynamic compliance (Cdyn) were calculated at isovolumetric and flow zero points, respectively, using an automated respiratory analyzer (Model 6; Buxco, Sharon, Conn.).

Animals were randomized and on Day 1 pretreatment values for PC50 were obtained for aerosolized adenosine. Antisense (HAdA1AS) or mismatched control (HAdA1MM) oligonucleotides were dissolved in sterile physiological saline at a concentration of 5000 ug (5 mg) per 1.0 ml. Animals were subsequently administered the aerosolized antisense or mismatch oligonucleotide via the intratracheal tube (approximately 5000 µg in a volume of 1.0 ml), twice daily for two days. Aerosols of either saline, adenosine, or antisense or mismatch oligonucleotides were generated by an ultrasonic nebulizer (DeVilbiss, Somerset, Pa.), producing aerosol droplets 80% of which were smaller than 5 µm in diameter.

In the first arm of the experiment, four randomly selected allergic rabbits were administered antisense oligonucleotide and four the mismatched control oligonucleotide. On the morning of the third day, PC50 values (the concentration of aerosolized adenosine in mg/ml required to reduce the dynamic compliance of the bronchial airway 50% from the baseline value) were obtained and compared to PC50 values obtained for these animals prior to exposure to oligonucleotide.

Following a 1 week interval, animals were crossed over, with those previously administered mismatch control oligonucleotide now administered antisense oligonucleotide, and those previously treated with antisense oligonucleotide now administered mismatch control oligonucleotide. Treatment methods and measurements were identical to those employed in the first arm of the experiment. It should be noted that in six of the eight animals treated with antisense oligonucleotide, adenosine-mediated bronchoconstriction could not be obtained up to the limit of solubility of adenosine, 20 mg/ml. For the purpose of calculation, PC50 values for these animals were set at 20 mg/ml. The values given therefore represent a minimum figure for antisense effectiveness. Actual effectiveness was higher. The results of this experiment are illustrated in Table 1.

TABLE 1

EFFECTS OF ADENOSINE $A_1$ RECEPTOR ANTISENSE OLIGO-
NUCLEOTIDE UPON PC50 VALUES IN ASTHMATIC RABBITS.

| Mismatch Control | | $A_1$ receptor Antisense oligonucleotide | |
|---|---|---|---|
| Pre oligonucleotide | Post oligonucleotide | Pre oligonucleotide | Post oligonucleotide |
| 3.56 ± 1.02 | 5.16 ± 1.93 | 2.36 ± 0.68 | >19.5 ± 0.34** |

Results are presented as the mean (N = 8) ± SEM. Significance was determined by repeated-measures analysis of variance (ANOVA), and Tukey's protected t test.
**Significantly different from all other groups, P < 0.01.

In both arms of the experiment, animals receiving the antisense oligonucleotide showed an order of magnitude increase in the dose of aerosolized adenosine required to reduce dynamic compliance of the lung by 50%. No effect of the mismatched control oligonucleotide upon PC50 values was observed. No toxicity was observed in any animal receiving either antisense or control inhaled oligonucleotide.

These results show clearly that the lung has exceptional potential as a target for antisense oligonucleotide-based therapeutic intervention in lung disease. They further show, in a model system which closely resembles human asthma, that downregulation of the adenosine $A_1$ receptor largely eliminates adenosine-mediated bronchoconstriction in asthmatic airways. Bronchial hyperresponsiveness in the allergic rabbit model of human asthma is an excellent endpoint for antisense intervention since the tissues involved in this response lie near to the point of contact with aerosolized oligonucleotides, and the model closely simulates an important human disease.

Example 4

Specificity of $A_1$-adenosine Receptor Antisense Oligonucleotide

At the conclusion of the crossover experiment of Example 3, airway smooth muscle from all rabbits was quantitatively analyzed for adenosine $A_1$ receptor number. As a control for the specificity of the antisense oligonucleotide, adenosine $A_2$ receptors, which should not have been affected, were also quantified.

Airway smooth muscle tissue was dissected from each rabbit and a membrane fraction prepared according to described methods (J. Kleinstein and H. Glossmann, *Naunyn-Schmiedeberg's Arch. Pharmacol.* 305, 191–200 (1978), with slight modifications. Crude plasma membrane preparations were stored at −70° C. until the time of assay. Protein content was determined by the method of Bradford (M. Bradford, *Anal. Biochem.* 72, 240–254 (1976)). Frozen plasma membranes were thawed at room temperature and were incubated with 0.2 U/ml adenosine deaminase for 30 minutes at 37° C. to remove endogenous adenosine. The binding of [$^3$H]DPCPX ($A_1$ receptor-specific) or [$^3$H]CGS-21680 ($A_2$ receptor-specific) was measured as previously described. S. Ali et al., *J. Pharmacol. Exp. Ther.* 268, 1328–1334 (1994); S. Ali et al., *Am. J. Physiol* 266, L271–277 (1994).

As illustrated in Table 2, animals treated with adenosine $A_1$ antisense oligonucleotide in the crossover experiment had a nearly 75% decrease in $A_1$ receptor number compared to controls, as assayed by specific binding of the $A_1$-specific antagonist DPCPX. There was no change in adenosine $A_2$ receptor number, as assayed by specific binding of the $A_2$ receptor-specific agonist 2-[p-(2-carboxyethyl)-phenethylamino]-5'-(N-ethylcarboxamido) adenosine (CGS-21680).

TABLE 2

SPECIFICITY OF ACTION OF ADENOSINE $A_1$ RECEPTOR
ANTISENSE OLIGONUCLEOTIDE.

| | Mismatch Control oligonucleotide | $A_1$ Antisense oligonucleotide |
|---|---|---|
| $A_1$-Specific Binding | 1105 ± 48** | 293 ± 18 |
| $A_2$-Specific Binding | 302 ± 22 | 442 ± 171 |

Results are presented as the mean (N = 8) ± SEM. Significance was determined by repeated-measures analysis of variance (ANOVA), and Tukey's protected t test.
**Significantly different from mismatch control, P < 0.01.

The foregoing examples are illustrative of the present invention, and are not to be construed as limiting thereof. The invention is defined by the following claims, with equivalents of the claims to be included therein.

That which is claimed is:

1. A pharmaceutical composition, comprising
an oligonucleotide (oligo) in aerosol form, which is effective for alleviating bronchoconstriction or lung inflammation when administered to a mammal, wherein the oligo is antisense to the initiation codon, the coding region or the 5' and 3' intronexon junctions of a gene encoding the adenoshie $A_1$ receptor or antisense to an adenosine $A_1$ receptor mRNA; and a pharmaceutical carrier.

2. The pharmaceutical composition of claim 1, wherein the oligo comprise at least one mononucleotide linking residue selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene(methyimino), methyleneoxy (methylimino) and phosphoramidate residues.

3. The pharmaceutical composition of claim 2, wherein the all mononucleotide linking residues of the oligo are selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene(methyimino), methyleneoxy (methylimino) and phosphoramidate residues.

4. The pharmaceutical composition of claim 1, wherein the antisense to the initiation codon of a gene encoding an adenosine $A_1$ receptor or antisense to an adenosinie $A_1$ receptor mRNA.

5. The pharmaceutical composition of claim 1, wherein the oligo is a DNA.

6. The pharmaceutical composition of claim 1, wherein the oligo is an RNA.

7. The pharmaceutical composition of claim 1, wherein the oligo is antisense to the intron-exon junction of an adenosine $A_1$ receptor gene or antisense to an adenosine $A_1$ receptor mRNA.

8. The pharmaceutical composition of claim 1, wherein the oligo comprises about 10 to up to about 60 mononucleotides.

9. The pharmaceutical composition of claim 7, wherein the oligo comprises about 18 up to about 21 mononucleotides.

10. The pharmaceutical composition of claim 1, wherein the oligo is antisense to the coding region of a gene encoding the adenosine $A_1$ receptor or antisense to an adenosine $A_1$ receptor mRNA.

11. The pharmaceutical composition of claim 1, wherein the oligo is

SEQ. ID NOS: 1 or 7 to 952; or

SEQ. ID NOS: 1 or 7 to 952, wherein at least one mononucleotide linking residue is selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene(methyimino), methyleneoxy (methylimino) and phosphoramidate residues.

12. The pharmaceutical composition of claim 11, wherein the oligo is selected from SEQ. ID NOS: 7 to 952; or SEQ. ID NOS: 7 to 952; wherein at least one mononucleotide linking residue is selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene(methyimino), methyleneoxy (methylimino) and phosphoramidate residues.

13. The pharmaceutical composition of claim 11, wherein the oligo has at least one phosphorothioate mononucleotide linking residue.

14. The pharmaceutical composition of claim 13, wherein all mononucleotide linking residues are phosphorothioate residues.

15. The pharmaceutical composition of claim 11, wherein the oligo is selected from SEQ. ID NOS: 1 or 7 to 952.

16. The pharmaceutical composition of claim 15, wherein the oligo is SEQ. ID NO: 7.

17. The pharmaceutical composition of claim 16, wherein the oligo is SEQ. ID NO: 7, wherein all momonucleotide linking residues are phosphorothioate residues.

18. The pharmaecutical composition of claim 11, wherein the oligo ia selected from SEQ. ID NOS: 1 or 7 to 952, wherein at least one mononucleotide linking residue is selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene(methyimino), methyleneoxy (methylimino) and phosphoramidate residues.

19. The pharmaceutical composition of claim 15, wherein the oligo is selected from SEQ. ID NOS: 8 to 952.

20. The pharmaceutical composition of claim 19, wherein the oligo is selected from SEQ. ID NOS; 8 to 952 wherein at least one mononucleotide linking residue is a phosphorothioate residue.

21. The pharmaceutical composition of claim 20, wherein all mononucleotide linking residues are phosphorothioate residues.

22. The pharmaceutical composition of claim 1, wherein the carrier is selected from the group consisting of solid and liquid carriers.

23. The pharmaceutical composition of claim 1, further comprising an agent selected from the group consisting of antioxidants, flavoring agents, volatile oils, buffering agents, dispersants, surfactants, propellants and preservatives.

24. The pharmaceutical composition of claim 1, wherein the oligo is present in an amount of about 0.1 to about 100% w/w of the composition.

25. The pharmaceutical composition of claim 24, wherein the oligo is present in an amount of about 0.1 up to about 40% w/w of the composition.

26. The pharmaceutical composition of claim 25, wherein the nucleic acid is present in an amount of about 0.1 up to about 20% w/w of the composition.

27. The pharmaceutical composition of claim 1, wherein the carrier comprises a hydrophobic carrier.

28. The pharmceutical composition of claim 27, wherein the carrier comprises lipid particles or vesicles.

29. The pharmaceutical composition of claim 28, wherein the vesicles comprise liposomes and the particles comprise microcrystals.

30. The pharmaceutical composition of claim 28, wherein the vesicles comprise liposomes which comprise the antisense oligo.

31. The pharmaceutical composition of claim 28, wherein the particles comprise a lipid selected from the group consisting of N-(1-(2,3-dioleoxyloxi) propyl)-N,N,N-trimethyl-ammoniommethylsulfate.

32. The pharmaceutical composition of claim 27, comprising liquid or solid respirable particles.

33. The pharmaceutical composition of claim 27, which is an aerosol composition.

34. The pharmaceutical composition of claim 1, comprised in a capsule or cartridge.

35. The pharmaceutical composition of claim 27, comprising solid particles of the oligo.

36. The pharmaceutical composition of claim 27, comprising a suspension or solution of the oligo.

37. The pharmaceutical composition of claim 36, wherein the oligo is suspended or dissolved in a solvent or mixture of solvents.

38. The pharmaceutical composition of claim 37, wherein the solvent is selected from the group consisting of chlorofluorocarbons or chlorofluorocarbons with co-solvents, and the pharmaceutical composition further comprises an agent selected from the group consisting of surfactants, antioxidants and flavoring agents.

39. The pharmaceutical composition of claim 35, which is comprised within a capsule or cartridge.

40. The pharmaceutical composition of claim 23, comprising a surfactant.

41. A method of treating an adenosine $A_1$ receptor mediated respiratory disease or condition associated with bronchoconstriction or lung inflammation, comprising administering directly to the respiration of a mammalian subject in need of such treatment an aerosol of the pharmaceutical composition of claim 1 comprising an amount of the oligo effective for alleviating bronchoconstriction and/or lung inflammation.

42. The method of claim 41, wherein the pharmaceutical composition comprises respirable particles comprising the oligo.

43. The method of claim 41, wherein the disease or condition comprises lung inflammation.

44. The method of claim 41, wherein the disease or condition comprises a respiratory disease or condition associated with bronoconstriction or lung inflammation.

45. The method of claim 41, wherein the disease or condition comprises asthma.

46. The method of claim 41, wherein the mammalian subject is non-human.

47. The method of claim 41, wherein the mammalian subject is a human.

48. The method of claim 41, wherein the oligo is administered in an amount of about 0.01 to about 150 mg/kg body weight.

49. The method of claim 48, wherein the oligo is administered in an amount of about 1 to about 100 mg/kg body weight.

50. The method of claim 49, wherein the oligo is administered in an amount of about 10 up to about 50 mg/kg body weight.

51. The method of claim 41, being a prophylactic method.

52. The method of claim 41, being a therapeutic method.

53. The method of claim 41, wherein the pharmaceutical composition further comprises an agent selected from the group consisting of antioxidants, flavoring agents, volatile oils, buffering agents, dispersants, surfactants, propellants and preservatives.

54. The method of claim 53, wherein the pharmaceutical composition comprises a surfactant.

55. The method of claim 41, wherein the oligo is antisense to the coding region or the initiation codon of a gene encoding the adenosine $A_1$ receptor or antisense to an adenosine $A_1$ receptor mRNA, wherein at least one mononucleotide linking residue is selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene(methyimino), methyleneoxy (methylimino) and phosphoramidate residues.

56. The method of claim 55, wherein all mononucleotide linking residues of the oligo are selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene(methyimino), methyleneoxy (methylimino) and phosphoramidate residues.

57. The method of claim 41, wheren the oligo is
SEQ. ID NOS: 1 or 7 to 952; or
SEQ. ID NOS: 1 or 7 to 952, wherein at least one mononucleotide linking residue is selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene(methyimino), methyleneoxy (methylimino) and phosphoramidate residues.

58. The method of claim 57, wherein the oligo is selected from
SEQ. ID NO: 7 to 952; or
SEQ. ID NO: 7 to 952, wherein at least one mononucleotide linking residue is selected from the group consisting of methyphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene(metthyimino), methyleneoxy (methylimino) and phosphoramidate residues.

59. The method of claim 58, wherein the oligo is SEQ. ID NOS: 1 or 7 to 952, wherein at least one mononucleotide linking residue is a phosphorothioate residue.

60. The method of claim 57, wherein all mononucleotide linking residues are phosphorothioate residues.

61. The method of claim 59, wherein the oligo is selected from SEQ. ID NOS: 7 to 952, wherein at least one mononucleotide linking residue is selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene (methyimino), methyleneoxy (methylimino) and phosphoramidate residues.

62. The method of claim 61, wherein the oligo is selected from SEQ. ID NOS: 8 to 952, wherein at least one mononucleotide linking residue is selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene (methyimino), methyleneoxy (methylimino) and phosphoramidate residues.

63. An in vivo method of delivering an oligonucleotide (oligo) to a target adenosine $A_1$ receptor polynucleotide, comprising administering into a malarian subject's respiration an aerosol of the composition of claim 1, comprising an amount of the adenosine $A_1$ receptor oligo effective to reach the target $A_1$ adenosine receptor polynucleotide.

64. The method of claim 63, wherein the aerosol comprises respirable oligo particles.

65. The method of claim 63, wherein the oligo is selected from the group consisting of oligos which are antisense to an intron-exon junction of an adenosine $A_1$ receptor gene or antisense to an adenosine $A_1$ mRNA; and antisense to an intron-exon junction of an adenosine $A_1$ receptor gene or antisense to an adenosine $A_1$ receptor mRNA, wherein the oligo comprises at least one mononucleotide linking residue selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonanide, sulfone, sulfite, sulfoxide, sulfide, hydroxylamine, methylene(methyimino), methylencoxy (methylimino) and phosphoramidate residues.

66. The method of claim 63, wherein the oligo is selected from oligos which are antisense to the coding region of a gene encoding an A1 adenosine receptor, or antisense to an A1 adenosine receptor mRNA; or oligos which are antisense to the coding region of a gene encoding an A1 adenosine receptor, or antisense to an A1 adenosine receptor mRNA, wherein at least one mononucleotide linking residue is selected from the group consisting of methylphosphonate, phosphotriester, phosphorothioate, phosphorodithioate, boranophosphate, formacetal, thioformacetal, thioether, carbonate, carbamate, sulfate, sulfonate, sulfamate, sulfonamide, sulfone, sulfite, sulfoxide, sulfide, hydroxylamine, methylene (methyimino), methyleneoxy (methylimino) and phosphoramidate residues.

67. The method of claim 63, wherein the oligo is delivered to alleviate a disease or condition associated with bronchoconstriction or lung inflammation.

68. The method of claim 67, wherein the disease or condition comprises asthma.

69. The method of claim 63, wherein the mammalian subject is a human.

70. The method of claim 63, wherein the mammalian subject is an non-human mammal.

71. The method of claim 63, wherein the oligo is administered in an amount of about 0.01 to about 150 mg/kg body weight.

72. The method of claim 71, wherein the oligo is administered in an amount of about 1 to about 100 mg/kg body weight.

73. The method of claim 72, wherein the oligo is administered in an amount of about 1 up to 50 mg/kg body weight.

74. The method of claim 67, being a prophylactic method.

75. The method of claim 67, being a therapeutic method.

76. The method of claim 63, wherein the composition further comprises an agent selected from the group consisting of antioxidants, flavoring agents, volatile oils, buffering agents, dispersants, surfactants, propellants and preservatives.

77. The method of claim 76, wherein the composition comprises a surfactant.

* * * * *